US008927009B2

(12) United States Patent
Tong et al.

(10) Patent No.: US 8,927,009 B2
(45) Date of Patent: Jan. 6, 2015

(54) ABT-263 CAPSULE

(75) Inventors: Ping Tong, Libertyville, IL (US); Deliang Zhou, Vernon Hills, IL (US); Geoff G. Z. Zhang, Vernon Hills, IL (US); Katherine R. Heemstra, Chicago, IL (US); Cristina M. Fischer, Wadsworth, IL (US); Nathaniel D. Catron, Vernon Hills, IL (US); Eric A. Schmitt, Libertyville, IL (US); Yeshwant D. Sanzgiri, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 288 days.

(21) Appl. No.: 12/974,154

(22) Filed: Dec. 21, 2010

(65) Prior Publication Data

US 2011/0159085 A1 Jun. 30, 2011

Related U.S. Application Data

(60) Provisional application No. 61/289,289, filed on Dec. 22, 2009.

(51) Int. Cl.
*A61K 9/48* (2006.01)
*A61K 31/5377* (2006.01)
*A61K 47/14* (2006.01)
*A61K 47/24* (2006.01)

(52) U.S. Cl.
CPC .......... *A61K 31/5377* (2013.01); *A61K 9/4858* (2013.01); *A61K 47/14* (2013.01); *A61K 47/24* (2013.01)
USPC ............................. 424/452; 264/4; 514/235.8

(58) Field of Classification Search
None
See application file for complete search history.

(56) References Cited

U.S. PATENT DOCUMENTS

| | | | |
|---|---|---|---|
| 5,536,729 A | 7/1996 | Waranis et al. | |
| 5,538,737 A | 7/1996 | Leonard et al. | |
| 5,559,121 A | 9/1996 | Harrison et al. | |
| 5,635,187 A | 6/1997 | Bathurst et al. | |
| 5,645,856 A | 7/1997 | Lacy et al. | |
| 5,665,379 A | 9/1997 | Herlof et al. | |
| 5,707,648 A | 1/1998 | Yiv | |
| 6,004,973 A | 12/1999 | Guitard et al. | |
| 6,267,985 B1 | 7/2001 | Chen et al. | |
| 6,309,663 B1 | 10/2001 | Patel et al. | |
| 6,451,339 B2 | 9/2002 | Patel et al. | |
| 6,464,987 B1 | 10/2002 | Fanara et al. | |
| 6,964,946 B1 | 11/2005 | Gutierrez-Rocca et al. | |
| 7,459,283 B2 | 12/2008 | Wertz et al. | |
| 7,842,681 B2 | 11/2010 | Elmore et al. | |
| 7,973,161 B2 | 7/2011 | Bruncko et al. | |
| 8,168,784 B2 | 5/2012 | Frnczyk, II et al. | |
| 2002/0055631 A1 | 5/2002 | Augeri et al. | |
| 2003/0236236 A1 | 12/2003 | Chen et al. | |
| 2005/0101628 A1 | 5/2005 | Jiao et al. | |
| 2005/0163835 A1 | 7/2005 | Gellert et al. | |
| 2005/0208082 A1 | 9/2005 | Papas et al. | |
| 2006/0177430 A1* | 8/2006 | Bhushan et al. | 424/94.1 |
| 2006/0183776 A9* | 8/2006 | Pratt | 514/319 |
| 2007/0027135 A1 | 2/2007 | Bruncko et al. | |
| 2007/0072860 A1 | 3/2007 | Bruncko et al. | |
| 2007/0104780 A1 | 5/2007 | Lipari et al. | |
| 2007/0161681 A1 | 7/2007 | Marfat et al. | |
| 2008/0085313 A1 | 4/2008 | Given et al. | |
| 2008/0182845 A1 | 7/2008 | Bardwell et al. | |
| 2009/0149461 A1 | 6/2009 | Krivoshik | |
| 2010/0233251 A1 | 9/2010 | Von Andrian et al. | |
| 2010/0278905 A1 | 11/2010 | Catron et al. | |
| 2010/0278921 A1 | 11/2010 | Fischer et al. | |
| 2010/0297194 A1 | 11/2010 | Catron et al. | |
| 2010/0305122 A1 | 12/2010 | Bruncko et al. | |
| 2010/0305125 A1 | 12/2010 | Borchardt et al. | |
| 2010/0323020 A1 | 12/2010 | Gokhale et al. | |
| 2011/0071151 A1 | 3/2011 | Zhang et al. | |

FOREIGN PATENT DOCUMENTS

| | | |
|---|---|---|
| CN | 1561201 A | 1/2005 |
| CN | 1706371 A | 12/2005 |
| CN | 101175738 A | 5/2008 |
| CN | 101325944 A | 12/2008 |
| CN | 101220008 A | 8/2010 |
| CN | 101798292 A | 8/2010 |
| EP | 1880715 A1 | 1/2008 |
| WO | 0057854 A2 | 10/2000 |
| WO | 0100175 A1 | 1/2001 |
| WO | 0224636 A2 | 3/2002 |
| WO | 2003028705 A1 | 4/2003 |
| WO | 2005049593 A2 | 6/2005 |
| WO | 2007040650 A2 | 4/2007 |

(Continued)

OTHER PUBLICATIONS

Lessene et al., "BCL-2 family antagonists for cancer therapy", Dec. 2008, Nature Reviews Drug Discovery, vol. 7, pp. 989-1000.*
Bruncko M., et al., "Studies Leading to Potent, Dual Inhibitors of Bcl-2 and Bcl-XL," Journal of Medicinal Chemistry, 2007, vol. 50 (4), pp. 641-662.
Hanahan D., et al., "The Hallmarks of Cancer," Cell, 2000, vol. 100 (1), pp. 57-70.
Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.

(Continued)

*Primary Examiner* — Robert A Wax
*Assistant Examiner* — Randeep Singh

(57) ABSTRACT

A pharmaceutical capsule comprises a shell having encapsulated therewithin a liquid solution of ABT-263 or a pharmaceutically acceptable salt thereof in a substantially non-ethanolic carrier that comprises as pharmaceutically acceptable excipients (a) at least one phospholipid, (b) at least one solubilizing agent for the at least one phospholipid, selected from the group consisting of glycols, glycerides and mixtures thereof, (c) at least one non-phospholipid surfactant and (d) at least one sulfur-containing antioxidant. The capsule is useful in treatment of a disease characterized by overexpression of one or more anti-apoptotic Bcl-2 family proteins, for example cancer.

36 Claims, 3 Drawing Sheets

(56) References Cited

FOREIGN PATENT DOCUMENTS

| WO | 2007043057 A2 | 4/2007 |
|---|---|---|
| WO | 2008124878 A1 | 10/2008 |
| WO | 2009073835 A1 | 6/2009 |
| WO | 2009155386 A1 | 12/2009 |
| WO | 2010127190 A1 | 11/2010 |
| WO | 2010127193 A1 | 11/2010 |
| WO | 2010127198 A1 | 11/2010 |
| WO | 2011034934 A1 | 3/2011 |

OTHER PUBLICATIONS

Tse, C. et al., "ABT-263: A Potent and Orally Bioavailable Bcl-2 Family Inhibitor," Cancer Research, 2008, vol. 68 (9), pp. 3421-3428—Including Supplementary Data.
International Search Report for Application No. PCT/US2010/061588, dated Feb. 18, 2011 (3 pages).
Berge et al., "Pharmaceutical Salts," Journal of Pharmaceutical Sciences, Review Article, 66(1): 1-19 (1977).
Wendt, Michael D., "Discovery of ABT-263, a Bcl-family protein inhibitor: observations on targeting a large protein-protein interaction," Expert Opinion Drug Discovery, 3(9): 1123-1143 (2008).
Caira, Mino R., "Crystalline Polymorphism of Organic Compounds," Topics in Current Chemistry, Department of Chemistry, University of Cape Town, Springer Verlag, Berlin, 198: 163-208 (1998).
Fiedler H. B., "Encyclopedia of Excipients: For Pharmaceuticals, Cosmetics and Related Areas," (Der Pharmazeutische Betrieb), 5th Edition, Editio-Cantor 2002 (6 pages).
Gould, Philip L., "Salt Selection for Basic Drugs," International Journal of Pharmaceutics, 33: 201-217 (1986).
Handbook of Pharmaceutical Excipients, 3rd edition. American Pharmaceutical Association, Arthur H. Kibbe, Editor (2000) Table of Contents.
Hovorka S.W., et al., "Oxidative degradation of pharmaceuticals: Theory, mechanisms and inhibition," Journal of Pharmaceutical Sciences, 90(3): 253-269 (2001).
Introduction to Physical Polymer Science, 2nd Edition, L.H. Sperling, Editor, John Wiley & Sons (1992).
Park et al., "Discovery of an orally bioavailable small molecule inhibitor of prosurvival B-cell lymphoma 2 proteins," Journal of Medicinal Chemistry, 51(21): 6902-6915 (2008).
Trotta et al., Stability of drug-carrier emulsions containing phosphatidylcholine mixtures, European Journal of Pharmaceutics and Biopharmaceutics 53: 203-208 (2002).
Brittain, Harry G. et al., "Effects of of Pharmaceutical Processing on Drug Polymorphs and Solvates", vol. 95, pp. 331-361.
Chawla et al., "Polymorphism of Pharmaceuticals: Challenges and Opportunities," www.expresspharmaonline.com/20031023/edito2.shtml, (Oct. 23, 2003) 3 pages.
Crowley, M. et al.; "Pharmaceutical Applications of Hot-Melt Extrusion: Part 1"; Drug Development and Industrial Pharmacy, vol. 33, 2007, pp. 909-926.
Holzelova, E. et al.; "Autoimmune Lymphoproliferative Syndrome with Somatic Fas Mutations", The New England Journal of Medicine, vol. 351, 2004, pp. 1409-1418.
International Search Report and Written Opinion of the International Searching Authority mailed on Dec. 13, 2010 regarding PCT/IB2010/001659 filed Jun. 8, 2010; 12 pages.
Supplemental International Search Report of the International Searching Authority mailed on Sep. 29, 2011 regarding PCT/IB2010/001659 filed Jun. 8, 2010, 3 page.
PCT International Search Report and Written Opinion of the International Searching Authority mailed on Jul. 12, 2010 regarding PCT/US2010/033072 filed on Apr. 30, 2010, 8 pages.
PCT International Search Report of the International Searching Authority mailed on Oct. 8, 2010 regarding PCT/US2010/033073 filed on Apr. 30, 2010, 4 pages.
PCT International Search Report of the International Searching Authority mailed on Oct. 19, 2010 regarding PCT/US2010/033074 filed on Apr. 30, 2010, 3 pages.
PCT International Search Report of the International Searching Authority mailed on Oct. 19, 2010 regarding PCT/US2010/033075 filed on Apr. 30, 2010, 3 pages.
PCT International Search Report of the International Searching Authority mailed on Oct. 19, 2010 regarding PCT/US2010/033085 filed on Apr. 30, 2010, 3 pages.
PCT International Search Report of the International Searching Authority mailed on Nov. 5, 2010 regarding PCT/US2010/038526 filed on Jun. 14, 2010, 4 pages.
PCT International Search Report of the International Searching Authority mailed on Nov. 30, 2010 regarding PCT/US2010/048949 filed on Sep. 15, 2010, 6 pages.
Klein, Cheri Enders. et al., "The Tablet Formulation of Lopinavir/Ritonavir Provides Similar Bioavailability to the Soft-Gelatin Capsule Formulation With Less Pharmacokinetic Variability and Diminished Food Effect", Journal of Acquired Immune Deficiency Syndromes, 2007, vol. 44; pp. 401-410.
Moschwitzer, Jan. et al., "Development of an intravenously injectable chemically stable aqueous omeprazole formulation using nanosuspension technology", European Journal of Pharamaceutics and Biopharmaceutics, vol. 58, 2004, pp. 615-619.
Paolini, Gaia V. et al, Global Mapping of Pharmacological Space, Nature Biotechnology, vol. 25, No. 7, Jul. 2006, pp. 805-815.
Puck, J. et al., "Immune Disorders Caused by Defects in the Caspase Cascade", Current Allergy and Asthma Reports, vol. 3, 2003, pp. 378-384.
Rengan R., et al., "Actin cytoskeletal function is spared, but apoptosis is increased, in WAS patient hematopoietic cells", Blood, vol. 95 (4) 2000, pp. 1283-1292.
Sharma, D.K. et al., "Solubility Enhancement Strategies for Poorly Water-Soluble Drugs in Solid Dispersions: A Review", Asian Journal of Pharmaceutis, 2007, vol. 1 (1), pp. 9-19.
Shimazaki, K. et al., "Evaluation of apoptosis as a prognostic factor in myelodysplastic syndromes"; British Journal of Haematology, vol. 110, 2000, pp. 584-590.
Sophie et al., "Synthesis of "Trioxaquantel" Derivatives as Potential New Antischistosomal Drugs", European Journal of Organic Chemistry, 2008, pp. 895-913.
SkyePharma—DissoCubes, www.skyepharma.com, 2010, pp. 1.
Extended European Search Report mail on Jun. 5, 2013 regarding European Patent Application No. 2515883 filed on Dec. 21, 2010; 7 pgs.
Wang, Guangjun et al., "An Efficient Synthesis of ABT-263, a Novel Inhibitor of Antiapoptotic Bcl-2 Proteins", Synthesis, 2008 (15), pp. 2398-2404.
U.S. Appl. No. 61/174,274, filed Apr. 30, 2009.
Anonymous: "Phosal(TM) 53 MCT" [Online] Feb. 2007, XP002601344 Phospholipid GmbH-American Lecithin Retrieved from the Internet: URL:http://www.americanlecithin.com/TDS/TDS_53MCT.PDF.
Brandrup et al., "Polymer Handbook," 2nd. Ed., John Wiley & Sons, 1975.

* cited by examiner

ABT-263 CAPSULE

This application claims priority benefit of U.S. Provisional Application Ser. No. 61/289,289 filed on Dec. 22, 2009, the entire disclosure of which is incorporated herein by reference.

Cross-reference is made to the following U.S. applications containing subject matter related to the present application: Ser. No. 12/770,122 titled "Lipid formulation of apoptosis promoter", filed on Apr. 29, 2010; Ser. No. 12/770,174 titled "Stabilized lipid formulation of apoptosis promoter", filed on Apr. 29, 2010; and Ser. No. 12/770,299 titled "Formulation for oral administration of apoptosis promoter", filed on Apr. 29, 2010.

FIELD OF THE INVENTION

The present invention relates to the apoptosis-promoting agent ABT-263, to formulations containing ABT-263, and to methods of use thereof for treating diseases characterized by overexpression of anti-apoptotic Bcl-2 family proteins. More particularly the invention relates to encapsulated formulations useful for oral administration of ABT-263 to a subject in need thereof.

BACKGROUND OF THE INVENTION

Evasion of apoptosis is a hallmark of cancer (Hanahan & Weinberg (2000) *Cell* 100:57-70). Cancer cells must overcome a continual bombardment by cellular stresses such as DNA damage, oncogene activation, aberrant cell cycle progression and harsh microenvironments that would cause normal cells to undergo apoptosis. One of the primary means by which cancer cells evade apoptosis is by up-regulation of anti-apoptotic proteins of the Bcl-2 family.

Compounds that occupy the BH3 binding groove of Bcl-2 proteins have been described, for example by Bruncko et al. (2007) *J. Med. Chem.* 50:641-662. These compounds have included N-(4-(4-((4'-chloro-(1,1'-biphenyl)-2-yl)methyl)piperazin-1-yl)benzoyl)-4-(1R)-3-(dimethylamino)-1-((phenylsulfanyl)methyl)propyl)amino)-3-nitrobenzene-sulfonamide, otherwise known as ABT-737, which has the formula:

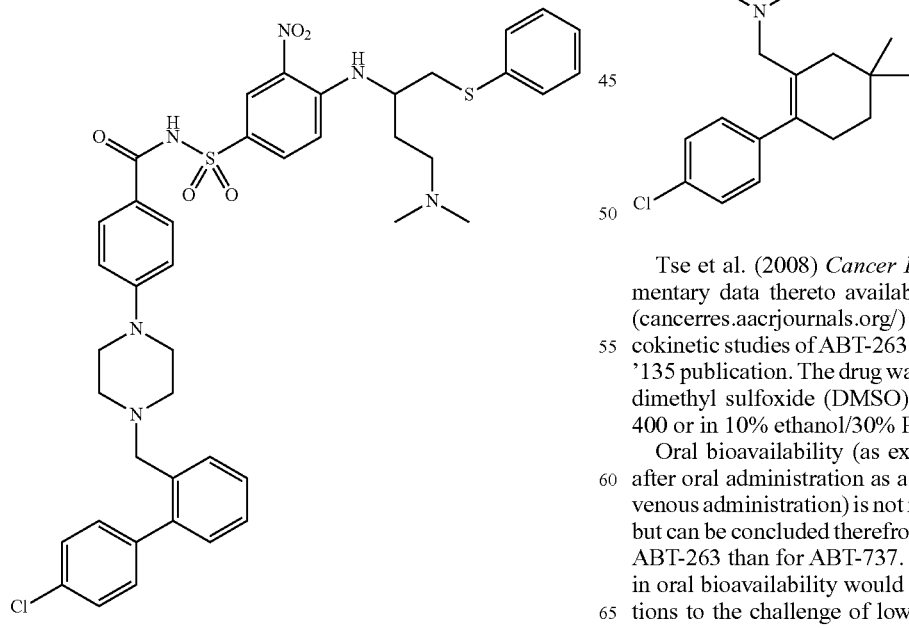

ABT-737 binds with high affinity (<1 nM) to proteins of the Bcl-2 family (specifically Bcl-2, Bcl-$X_L$ and Bcl-w). It exhibits single-agent activity against small-cell lung cancer (SCLC) and lymphoid malignancies, and potentiates pro-apoptotic effects of other chemotherapeutic agents. ABT-737 and related compounds, and methods to make such compounds, are disclosed in U.S. Patent Application Publication No. 2007/0072860 of Bruncko et al.

More recently, a further series of compounds has been identified having high binding affinity to Bcl-2 family proteins. These compounds, and methods to make them, are disclosed in U.S. Patent Application Publication No. 2007/0027135 of Bruncko et al. (herein "the '135 publication"), incorporated by reference herein in its entirety, and can be seen from their formula to be structurally related to ABT-737.

One compound, identified as "Example 1" in the '135 publication, is N-(4-(4-(2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, otherwise known as ABT-263. This compound has a molecular weight of 974.6 g/mol and has the formula:

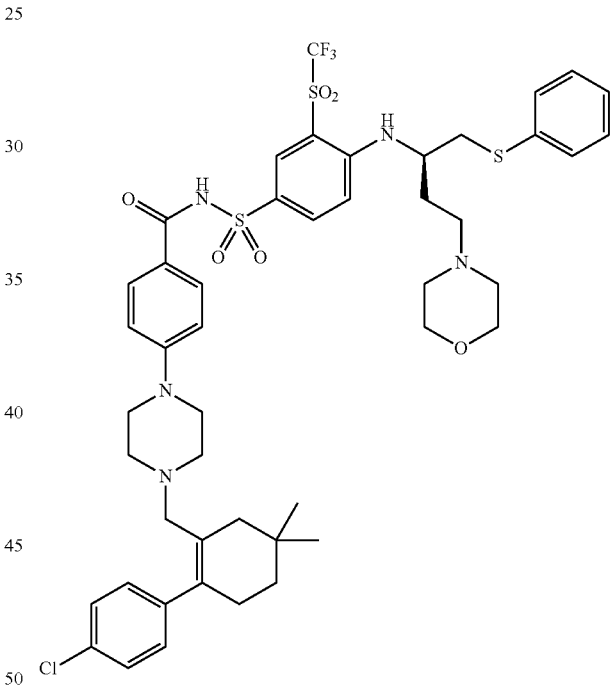

Tse et al. (2008) *Cancer Res.* 68:3421-3428 and supplementary data thereto available at Cancer Research Online (cancerres.aacrjournals.org/) have reported animal pharmacokinetic studies of ABT-263, synthesized as described in the '135 publication. The drug was formulated in solution in 10% dimethyl sulfoxide (DMSO) in polyethylene glycol (PEG) 400 or in 10% ethanol/30% PEG400/60% Phosal 50 PG™.

Oral bioavailability (as expressed, for example, by AUC after oral administration as a percentage of AUC after intravenous administration) is not reported in the '135 publication, but can be concluded therefrom to be substantially greater for ABT-263 than for ABT-737. However, further improvement in oral bioavailability would be advantageous. Various solutions to the challenge of low oral bioavailability have been proposed in the art. For example, U.S. Pat. No. 5,645,856 to Lacy et al. proposes formulating a hydrophobic drug with (a)

an oil, (b) a hydrophilic surfactant and (c) a lipophilic surfactant that substantially reduces an inhibitory effect of the hydrophilic surfactant on in vivo lipolysis of the oil, such lipolysis being said to be a factor promoting bioavailability of the drug. Among numerous classes of hydrophilic surfactants listed are phospholipids such as lecithins.

U.S. Pat. No. 6,267,985 to Chen & Patel is directed, inter alia, to a pharmaceutical composition comprising (a) a triglyceride, (b) a carrier comprising at least two surfactants, one of which is hydrophilic, and (c) a therapeutic agent capable of being solubilized in the triglyceride, the carrier or both. It is specified therein that the triglyceride and the surfactants must be present in amounts providing a clear aqueous dispersion when the composition is mixed with an aqueous solution under defined conditions. Among extensive separate lists of exemplary ingredients, mention is made of "glyceryl tricaprylate/caprate" as a triglyceride, and phospholipids including phosphatidylcholine as surfactants.

U.S. Pat. No. 6,451,339 to Patel & Chen mentions disadvantages of presence of triglycerides in such compositions, and proposes otherwise similar compositions that are substantially free of triglycerides, but that likewise provide clear aqueous dispersions.

U.S. Pat. No. 6,309,663 to Patel & Chen proposes pharmaceutical compositions comprising a combination of surfactants said to enhance bioabsorption of a hydrophilic therapeutic agent. Phospholipids such as phosphatidylcholine are again listed among exemplary surfactants.

U.S. Pat. No. 6,464,987 to Fanara et al. proposes a fluid pharmaceutical composition comprising an active substance, 3% to 55% by weight of phospholipid, 16% to 72% by weight of solvent, and 4% to 52% by weight of fatty acid. Compositions comprising Phosal 50 PG™ (primarily comprising phosphatidylcholine and propylene glycol), in some cases together with Phosal 53 MCT™ (primarily comprising phosphatidylcholine and medium chain triglycerides), are specifically exemplified. Such compositions are said to have the property of gelling instantaneously in presence of an aqueous phase and to allow controlled release of the active substance.

U.S. Pat. No. 5,538,737 to Leonard et al. proposes a capsule containing a water-in-oil emulsion wherein a water-soluble drug salt is dissolved in the water phase of the emulsion and wherein the oil phase comprises an oil and an emulsifying agent. Among oils mentioned are medium chain triglycerides; among emulsifying agents mentioned are phospholipids such as phosphatidylcholine. Phosal 53 MCT™, which contains phosphatidylcholine and medium chain triglycerides, is reportedly used according to various examples therein.

U.S. Pat. No. 5,536,729 to Waranis & Leonard proposes an oral formulation comprising rapamycin, at a concentration of about 0.1 to about 50 mg/ml, in a carrier comprising a phospholipid solution. It is stated therein that a preferred formulation can be made using Phosal 50 PG™ as the phospholipid solution. An alternative phospholipid solution mentioned is Phosal 50 MCT™.

U.S. Pat. No. 5,559,121 to Harrison et al. proposes an oral formulation comprising rapamycin, at a concentration of about 0.1 to about 100 mg/ml, in a carrier comprising N,N-dimethylacetamide and a phospholipid solution. Examples of the more preferred embodiments are shown to be prepared using Phosal 50 PG™. An alternative phospholipid solution mentioned is Phosal 50 MCT™.

U.S. Patent Application Publication No. 2007/0104780 of Lipari et al. discloses that a small-molecule drug (defined therein as having molecular weight, excluding counterions in the case of salts, not greater than about 750 g/mol, typically not greater than about 500 g/mol) having low water solubility can be formulated as a solution in a substantially non-aqueous carrier comprising at least one phospholipid and a pharmaceutically acceptable solubilizing agent. The solution, when mixed with an aqueous phase, is said to form a non-gelling, substantially non-transparent liquid dispersion. Illustratively, formulations of N-(4-(3-amino-1H-indazol-4-yl)phenyl)-N'-(2-fluoro-5-methylphenyl)urea (the protein tyrosine kinase inhibitor ABT-869) comprising Phosal 53 MCT™ and other ingredients are described therein.

Recently a clinical study of ABT-263 has been disclosed in U.S. Patent Application Publication No. 2009/0149461 of Krivoshik, which is incorporated by reference herein in its entirety without admission that it constitutes prior art to the present invention. The formulation administered is described therein as a "powder for oral solution (2.0 grams/bottle base equivalent, 25 mg/ml when mixed)" and the diluents for constitution are identified as "Phosal® 53 medium chain triglyceride (MCT), 120 grams/bottle" and "alcohol (ethanol), dehydrated, USP/EP/JP 200 proof".

A particular type of disease for which improved therapies are needed is non-Hodgkin's lymphoma (NHL). NHL is the sixth most prevalent type of new cancer in the U.S. and occurs primarily in patients 60-70 years of age. NHL is not a single disease but a family of related diseases, which are classified on the basis of several characteristics including clinical attributes and histology.

One method of classification places different histological subtypes into two major categories based on natural history of the disease, i.e., whether the disease is indolent or aggressive. In general, indolent subtypes grow slowly and are generally incurable, whereas aggressive subtypes grow rapidly and are potentially curable. Follicular lymphomas are the most common indolent subtype, and diffuse large-cell lymphomas constitute the most common aggressive subtype. The oncoprotein Bcl-2 was originally described in non-Hodgkin's B-cell lymphoma.

Treatment of follicular lymphoma typically consists of biologically-based or combination chemotherapy. Combination therapy with rituximab, cyclophosphamide, doxorubicin, vincristine and prednisone (R-CHOP) is routinely used, as is combination therapy with rituximab, cyclophosphamide, vincristine and prednisone (RCVP). Single-agent therapy with rituximab (targeting CD20, a phosphoprotein uniformly expressed on the surface of B-cells) or fludarabine is also used. Addition of rituximab to chemotherapy regimens can provide improved response rate and increased progression-free survival.

Radioimmunotherapy agents, high-dose chemotherapy and stem cell transplants can be used to treat refractory or relapsed non-Hodgkin's lymphoma. Currently, there is not an approved treatment regimen that produces a cure, and current guidelines recommend that patients be treated in the context of a clinical trial, even in a first-line setting.

First-line treatment of patients with aggressive large B-cell lymphoma typically consists of rituximab, cyclophosphamide, doxorubicin, vincristine and prednisone (R-CHOP), or dose-adjusted etoposide, prednisone, vincristine, cyclophosphamide, doxorubicin and rituximab (DA-EPOCH-R).

Most lymphomas respond initially to any one of these therapies, but tumors typically recur and eventually become refractory. As the number of regimens patients receive increases, the more chemotherapy-resistant the disease becomes. Average response to first-line therapy is approximately 75%, 60% to second-line, 50% to third-line, and about 35-40% to fourth-line therapy. Response rates approaching 20% with a single agent in a multiple relapsed setting are considered positive and warrant further study.

Other neoplastic diseases for which improved therapies are needed include leukemias such as chronic lymphocytic leukemia (like NHL, a B-cell lymphoma) and acute lymphocytic leukemia.

Chronic lymphoid leukemia (CLL) is the most common type of leukemia. CLL is primarily a disease of adults, more than 75% of people newly diagnosed being over the age of 50, but in rare cases it is also found in children. Combination chemotherapies are the prevalent treatment, for example fludarabine with cyclophosphamide and/or rituximab, or more complex combinations such as CHOP or R-CHOP.

Acute lymphocytic leukemia, also known as acute lymphoblastic leukemia (ALL), is primarily a childhood disease, once with essentially zero survival but now with up to 75% survival due to combination chemotherapies similar to those mentioned above. New therapies are still needed to provide further improvement in survival rates.

Current chemotherapeutic agents elicit their antitumor response by inducing apoptosis through a variety of mechanisms. However, many tumors ultimately become resistant to these agents. Bcl-2 and Bcl-$X_L$ have been shown to confer chemotherapy resistance in short-term survival assays in vitro and, more recently, in vivo. This suggests that if improved therapies aimed at suppressing the function of Bcl-2 and Bcl-$X_L$ can be developed, such chemotherapy-resistance could be successfully overcome.

SUMMARY OF THE INVENTION

Hitherto, the only ABT-263 formulations disclosed as being useful for oral administration have been dilute liquids, including for example a solution of ABT-263 in 10% DMSO in PEG 400 or in 10% ethanol/30% PEG 400/60% Phosal 50 PG™, as administered by Tse et al. (2008), supra, or a 25 mg/ml solution of ABT-263 in Phosal 53 MCT™ and ethanol as disclosed in above-cited U.S. Patent Application Publication No. 2009/0149461 ("the '461 publication").

A discrete dosage form such as a capsule has advantages over a liquid in that the dose of drug is precisely pre-metered, the dosage form is easier to administer, enabling enhanced patient compliance, and a longer storage life is possible. Additionally, if the active ingredient or any excipient has an unpleasant taste, encapsulation of the formulation avoids this becoming an issue for the patient. It is known to encapsulate liquid formulations, for example in gelatin capsules; however, ABT-263 presents challenges in this regard.

First, typical unit doses of ABT-263 for most indications are relatively high (up to about 500 mg or even higher), which means that a dilute solution of ABT-263 such as the 25 mg/ml solution provided by the '461 publication cannot conveniently be presented in capsule form. Even a 200 mg dose would require 8 large (1 ml) capsules each containing 25 mg ABT-263. The poor solubility of ABT-263 in most pharmaceutically acceptable solvents has meant that no more concentrated solution showing acceptable storage-stability has hitherto been developed.

Second, although ABT-263 can be dissolved in phospholipid-based products such as Phosal 50 PG™ and Phosal 53 MCT™, the resulting solutions are highly viscous unless a viscosity-lowering agent such as ethanol is added. Ethanol and other viscosity lowering agents such as glycerol are not compatible with most capsule shell materials, particularly hard capsule shell materials such as a hard gelatin capsule shell.

Third, it has been found that ABT-263 is susceptible to oxidation to form degradation products including sulfoxides. This is not necessarily a serious problem for a liquid formulation that can be prepared extemporaneously, but for a pre-manufactured dosage form such as a capsule, oxidative degradation can mean an unacceptably short storage life. Thus it is important to include an antioxidant in a liquid formulation of ABT-263 for encapsulation; but as shown herein many commonly used antioxidants are ineffective to prevent formation of sulfoxides in ABT-263 formulations.

It has now been found that the challenges of providing a pharmaceutically acceptable liquid-filled capsule formulation of ABT-263 can be met by practice of the invention described herein.

In one embodiment, the present invention provides a pharmaceutical capsule comprising a capsule shell having encapsulated therewithin, in an amount not greater than about 1000 mg per capsule, a liquid solution of ABT-263 or a pharmaceutically acceptable salt thereof at an ABT-263 free-base equivalent concentration of at least about 40 mg/ml in a substantially non-ethanolic carrier that comprises as pharmaceutically acceptable excipients:

(a) at least one phospholipid,
(b) at least one solubilizing agent for the at least one phospholipid, selected from the group consisting of glycols, glycolides, glycerides and mixtures thereof,
(c) at least one non-phospholipid surfactant, and
(d) at least one sulfur-containing antioxidant in an amount effective to reduce oxidative degradation of ABT-263 upon storage.

In a more particular embodiment, the ABT-263 is present in the capsule in free-base as opposed to salt form.

In another more particular embodiment, the sulfur-containing antioxidant is poorly lipid-soluble; thus, as a result of introduction of the antioxidant as an aqueous stock solution, the encapsulated liquid solution according to this embodiment contains water. Presence of too much water can threaten physical stability of a liquid lipid-based solution, and can also increase rate of sulfoxide formation, negating the benefit of antioxidant addition. Importantly, therefore, the encapsulated liquid solution according to the present embodiment contains no more than about 1% by weight water.

The limitation on amount of sulfur-containing antioxidant imposed by the limitation on amount of water creates a further challenge. Typically, sulfur-containing antioxidants diminish formation of sulfoxide by-products of a drug by acting as competitive substrates for oxidative species such as peroxides; such mode of action generally requires that the antioxidant be present in an amount at least approaching molar equivalence to the amount of drug. Surprisingly, the present inventors have found that at molar ratios as low as 1:20 or even lower with respect to concentration of ABT-263, certain sulfur-containing antioxidants are remarkably effective in diminishing rate of sulfoxide formation under a variety of storage conditions. Suitable sulfur-containing antioxidants according to the present embodiment include without limitation sulfites, bisulfites, metabisulfites and thiosulfates.

Illustratively, a prototype capsule of the present embodiment comprises a size 0 hard gelatin capsule shell having encapsulated therewithin a liquid solution that comprises:

about 50 mg ABT-263 free base,
about 150 mg phosphatidylcholine,
about 75 mg medium-chain triglycerides,
about 90 mg medium-chain mono- and diglycerides,
about 90 mg polysorbate 80 surfactant,
about 0.25 mg sodium or potassium metabisulfite, about 0.025 mg EDTA (ethylene diamine tetraacetic acid, a chelating agent) or salt thereof, and about 2.5 mg water.

In another embodiment, the present invention provides a process for preparing the capsule as described above, comprising:

dissolving an API (active pharmaceutical ingredient) that consists essentially of the ABT-263 or salt thereof in at least the phospholipid and solubilizing agent to provide a lipid solution, admixing the non-phospholipid surfactant with the solubilizing agent or lipid solution, dissolving the poorly lipid-soluble sulfur-containing antioxidant in water to prepare an aqueous stock solution, admixing the aqueous stock solution with the lipid solution to provide a liquid solution for encapsulation, and encapsulating the liquid solution in a capsule shell.

In yet another embodiment, the present invention provides a method for treating a disease characterized by apoptotic dysfunction and/or overexpression of an anti-apoptotic Bcl-2 family protein, comprising orally administering to a subject having the disease a therapeutically effective amount of ABT-263 formulated as a capsule as described herein. Examples of such a disease include many neoplastic diseases including cancers. A specific illustrative type of cancer that can be treated according to the present method is non-Hodgkin's lymphoma. Another specific illustrative type of cancer that can be treated according to the present method is chronic lymphocytic leukemia (CLL). Yet another specific illustrative type of cancer that can be treated according to the present method is acute lymphocytic leukemia (ALL), for example in a pediatric patient.

In yet another embodiment, the present invention provides a method for maintaining in bloodstream of a human cancer patient, for example a patient having non-Hodgkin's lymphoma, CLL or ALL, a therapeutically effective plasma concentration of ABT-263 and/or one or more metabolites thereof, comprising administering to the subject one to a plurality of capsules comprising ABT-263 formulated as described herein, in a dosage amount of about 50 to about 1000 mg ABT-263 per day, at an average dosage interval of about 3 hours to about 7 days.

According to the above methods, the capsule administered can illustratively be the prototype capsule described above, or another capsule of the present invention that is orally substantially bioequivalent thereto.

Additional embodiments of the invention, including more particular aspects of those provided above, will be found in, or will be evident from, the detailed description that follows.

DETAILED DESCRIPTION

Figure 1:
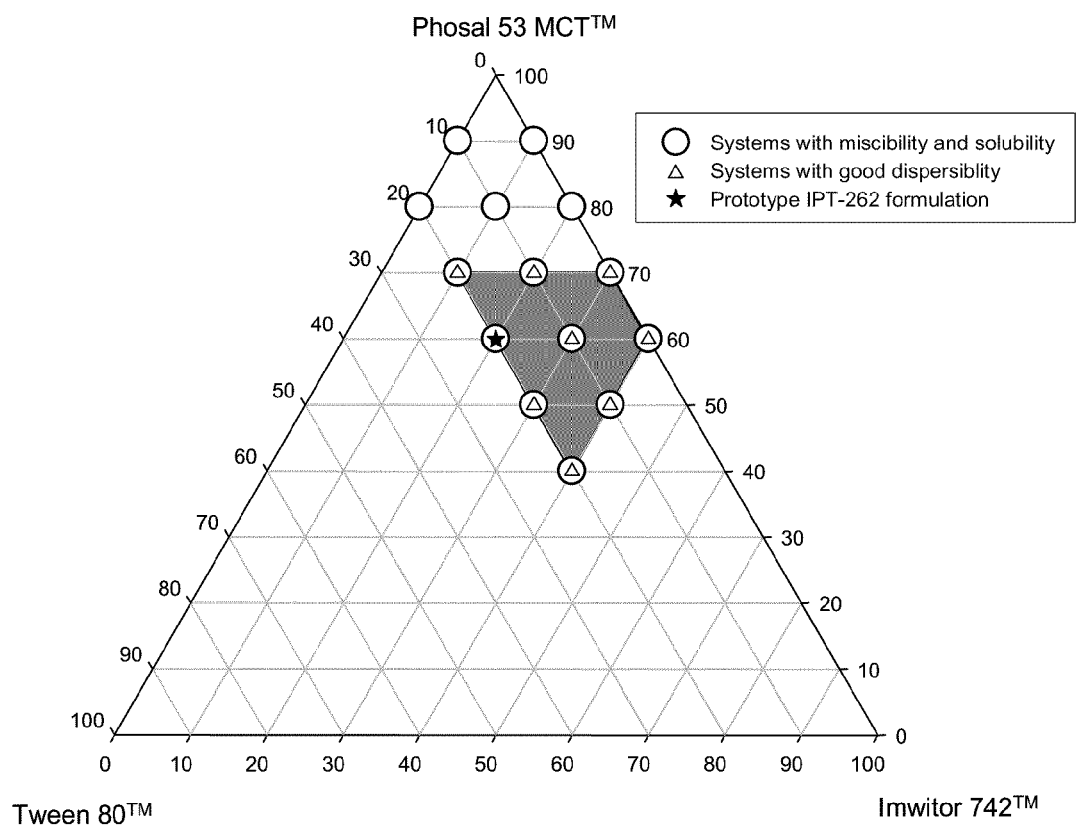
FIG. 1 is a schematic phase diagram of ABT-263 free base solutions in ternary "IPT" lipid systems as described in Example 8. The shaded portion of the diagram represents an area of optimized formulation composition.

The present invention provides a liquid-filled capsule formulation of ABT-263 or a salt thereof that is suitable for oral administration. The terms "oral administration" and "orally administered" herein refer to administration to a subject per os (p.o.), that is, administration wherein the composition is immediately swallowed, for example with the aid of a suitable volume of water or other potable liquid. "Oral administration" is distinguished herein from intraoral administration, e.g., sublingual or buccal administration or topical administration to intraoral tissues such as periodontal tissues, that does not involve immediate swallowing of the composition.

"ABT-263" herein refers to the compound N-(4-(4-(2-(4-chlorophenyl)-5,5-dimethyl-1-cyclohex-1-en-1-yl)methyl)piperazin-1-yl)benzoyl)-4-(1R)-3-(morpholin-4-yl)-1-((phenylsulfanyl)methyl)propyl)amino)-3-((trifluoromethyl)sulfonyl)benzenesulfonamide. In its parent-compound form, ABT-263 has the formula:

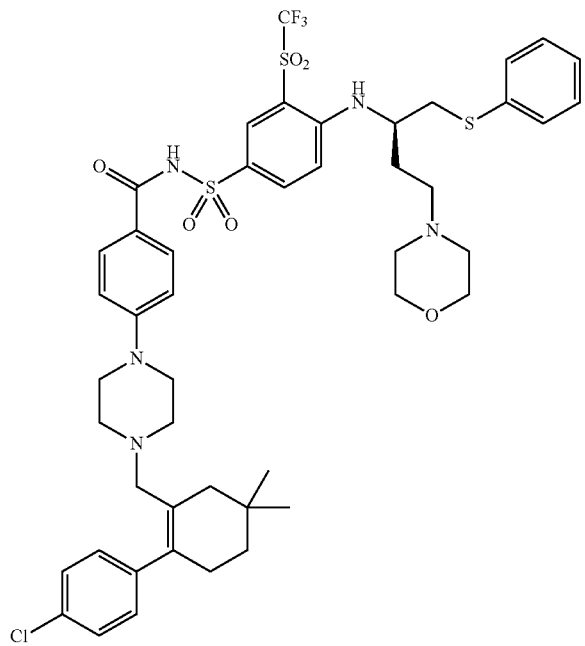

In some embodiments, ABT-263 is present in the formulation in its parent-compound form. The term "free base" is used for convenience herein to refer to the parent compound, while recognizing that the parent compound is, strictly speaking, zwitterionic and thus does not always behave as a true base.

ABT-263 may form acid addition salts, basic addition salts or zwitterions. Salts of compounds of Formula I can be prepared during isolation or following purification of the compounds. Acid addition salts are those derived from reaction of a ABT-263 with an acid. For example, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetate, trifluoroacetate, para-toluenesulfonate and undecanoate salts of ABT-263 can be used in a composition of the invention. Basic addition salts including those derived from reaction of ABT-263 with the bicarbonate, carbonate, hydroxide or phosphate of cations such as lithium, sodium, potassium, calcium and magnesium can likewise be used.

ABT-263 has at least two protonatable nitrogen atoms and is consequently capable of forming acid addition salts with more than one, for example about 1.2 to about 2, about 1.5 to about 2 or about 1.8 to about 2, equivalents of acid per equivalent of ABT-263.

Illustratively, bis-salts of ABT-263 can be formed including, for example, bis-hydrochloride (bis-HCl) and bis-hydrobromide (bis-HBr) salts.

For example, ABT-263 bis-HCl, represented by the formula

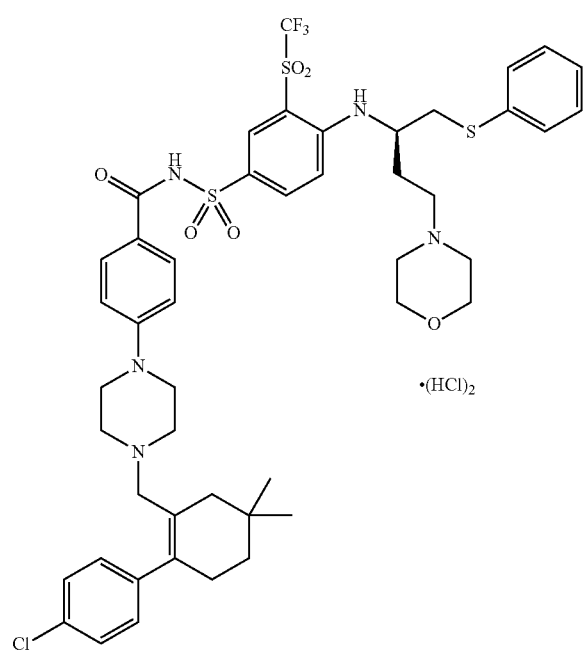

can be prepared by a variety of processes, for example a process that can be outlined as follows.

ABT-263 free base is prepared, illustratively as described in Example 1 of above-cited U.S. Patent Application Publication No. 2007/0027135, the entire disclosure of which is incorporated by reference herein. A suitable weight of ABT-263 free base is dissolved in ethyl acetate. A solution of hydrochloric acid in ethanol (for example about 4.3 kg HCl in 80 g EtOH) is added to the ABT-263 solution in an amount providing at least 2 mol HCl per mol ABT-263 and sufficient EtOH (at least about 20 vol) for crystallization of the resulting ABT-263 bis-HCl salt. The solution is heated to about 45° C. with stirring and seeds are added as a slurry in EtOH. After about 6 hours, the resulting slurry is cooled to about 20° C. over about 1 hour and is mixed at that temperature for about 36 hours. The slurry is filtered to recover a crystalline solid, which is an ethanol solvate of ABT-263 bis-HCl. Drying of this solid under vacuum and nitrogen with mild agitation for about 8 days yields white desolvated ABT-263 bis-HCl crystals. This material is suitable for preparation of an ABT-263 bis-HCl formulation of the present invention.

Thus a capsule of the present invention comprises ABT-263 free base or a pharmaceutically acceptable salt thereof, for example ABT-263 bis-HCl. In a more particular embodiment, the composition comprises ABT-263 free base.

As indicated above, ABT-263 free base can be prepared by a process as described in Example 1 of the above-cited '135 publication. The product of this process is an amorphous, glassy solid. A powder can be prepared from this product, for example by freeze-drying, spray-drying or precipitation techniques. Such a powder can be used as API in preparing a capsule of the present invention; however, it will generally be found preferable to use a crystalline form of ABT-263 free base as API. Such crystalline forms include solvates and solvent-free crystalline forms.

Solvates of ABT-263 free base can be prepared as described below. The starting product can be any solid-state form of ABT-263 free base, including the amorphous form prepared according to the '135 publication.

A measured amount of ABT-263 free base (as indicated, any solid-state form can be used) is suspended in any of a number of solvents or solvent mixtures, including without limitation 2-propanol, 1-propanol, ethyl acetate/ethanol 1:3 v/v, methyl acetate/hexanes 1:1 v/v, chloroform, methanol, 1,4-dioxane/hexanes 1:2 v/v, toluene and benzene. The resulting suspension is agitated at ambient temperature, while protected from light. After a period of time sufficient to permit solvation of ABT-263 free base in each case, crystals are harvested by filter centrifugation. The resulting solvates can be characterized by powder X-ray diffraction (PXRD), for example using a G3000 diffractometer (Inel Corp., Artenay, France) equipped with a curved position-sensitive detector and parallel-beam optics. The diffractometer is operated with a copper anode tube (1.5 kW fine focus) at 40 kV and 30 mA. An incident-beam germanium monochromator provides monochromatic radiation. The diffractometer is calibrated using an attenuated direct beam at one-degree intervals. Calibration is checked using a silicon powder line position reference standard (NIST 640c). The instrument is computer-controlled using Symphonix software (Inel Corp., Artenay, France) and the data are analyzed using Jade software (version 6.5, Materials Data, Inc., Livermore, Calif.). The sample is loaded onto an aluminum sample holder and leveled with a glass slide.

Desolvation of an ethyl acetate/ethanol solvate, for example by air-drying, provides a solvent-free crystalline form of ABT-263 free base. PXRD peaks for Form I ABT-263 free base are listed in Table 1. A PXRD pattern having peaks substantially as indicated therein can be used to identify crystalline ABT-263 free base, more particularly Form I ABT-263 free base. The phrase "substantially as indicated" in the present context means having peaks that are not shifted more than about 0.2° 2θ from the indicated position.

TABLE 1

| PXRD peak listing: solvent-free crystal polymorph Form I ABT-263 free base |
|---|
| Peak Position (° 2θ) |
| 6.21 |
| 6.72 |
| 9.66 |
| 10.92 |
| 11.34 |
| 12.17 |
| 14.28 |
| 16.40 |
| 16.95 |
| 17.81 |
| 18.03 |
| 18.47 |
| 19.32 |
| 20.10 |
| 21.87 |

Desolvation of most solvates, including 1-propanol, 2-propanol, methanol, benzene, toluene, dioxane/hexanes, methyl acetate/hexanes and chloroform solvates, provides a solvent-free crystalline form of ABT-263 free base that is shown by PXRD to be identical to the crystalline form produced by desolvation of the ethyl acetate/ethanol solvate.

Desolvation of pyridine and anisole solvates provides a solvent-free crystalline form of ABT-263 free base that is shown by PXRD to be different from the form produced by desolvation of the ethyl acetate/ethanol solvate. The crystalline form derived from desolvation of the pyridine or anisole solvate is designated Form II. PXRD peaks for Form II ABT-263 free base are listed in Table 2. A PXRD pattern having peaks substantially as indicated therein can be used to identify crystalline ABT-263 free base, more particularly Form II ABT-263 free base.

TABLE 2

PXRD peak listing: solvent-free crystal polymorph Form II ABT-263 free base

| Peak Position (° 2θ) |
| --- |
| 5.79 |
| 8.60 |
| 9.34 |
| 10.79 |
| 11.36 |
| 11.59 |
| 12.76 |
| 13.23 |
| 13.73 |
| 14.01 |
| 14.72 |
| 15.00 |
| 16.28 |
| 17.07 |
| 17.48 |
| 18.75 |
| 19.34 |
| 19.71 |
| 20.56 |
| 21.35 |

PXRD peaks especially diagnostic for Form I ABT-263 free base, in particular for distinguishing Form I from Form II, include the peaks at 6.21, 6.72, 12.17, 18.03 and 20.10° 2 θ, in each case ±0.2° 2 θ. In one embodiment, Form I ABT-263 free base is characterized at least by a peak at any one or more of these positions. In another embodiment, Form I ABT-263 free base is characterized at least by a peak at each of these positions. In yet another embodiment, Form I ABT-263 free base is characterized by a peak at each of the positions shown in Table 1.

PXRD peaks especially diagnostic for Form II ABT-263 free base, in particular for distinguishing Form II from Form I, include the peaks at 5.79, 8.60, 12.76, 15.00 and 20.56° 2 θ, in each case ±0.2° 2 θ. In one embodiment, Form II ABT-263 free base is characterized at least by a peak at any one or more of these positions. In another embodiment, Form II ABT-263 free base is characterized at least by a peak at each of these positions. In yet another embodiment, Form II ABT-263 free base is characterized by a peak at each of the positions shown in Table 2.

Any of the crystalline forms of ABT-263 free base, including solvated forms, can be useful as API for preparation of a capsule of the present invention. However, solvent-free forms such as Form I and Form II are generally preferred for this purpose.

Dosage amounts are expressed herein as free-base equivalent amounts unless the context requires otherwise. Typically, a unit dose (the amount administered at a single time), which can be administered at an appropriate frequency, e.g., twice daily to once weekly, is about 25 to about 1,000 mg, more typically about 50 to about 500 mg, for example about 50, about 100, about 150, about 200, about 250, about 300, about 350, about 400, about 450 or about 500 mg. A unit dose can be deliverable in a single capsule or a plurality of capsules, for example 1 to about 10 capsules, more typically 1 to about 5 capsules.

The higher the unit dose, the more desirable it becomes to select a blend of excipients that permits a relatively high concentration of the drug in solution therein. A suitable concentration of ABT-263 is at least about 40 mg/ml, e.g., about 50 to about 200 mg/ml, for example about 50, about 75, about 100, about 125, about 150 or about 200 mg/ml. On a weight/weight basis, a suitable concentration of ABT-263 is at least about 4%, e.g., about 5% to about 20%, for example about 5%, about 7.5%, about 10%, about 12.5%, about 15% or about 20% by weight.

In a capsule of the invention, ABT-263 is "in solution" in the encapsulated liquid. This will be understood to mean that substantially all of the ABT-263 is in solution, i.e., no substantial portion, for example no more than about 2%, or no more than about 1%, of the ABT-263 is in solid (e.g., crystalline) form, whether dispersed, for example in the form of a suspension, or not. In practical terms, this means that the ABT-263 must normally be formulated at a concentration below its limit of solubility in the blend of excipients used. It will be understood that the limit of solubility can be temperature-dependent, thus selection of a suitable concentration should take into account the range of temperatures to which the composition is likely to be exposed in normal storage, transport and use.

The encapsulated liquid is "substantially non-ethanolic", i.e., having no ethanol, or having an amount of ethanol that is small enough to be, in practical terms, essentially non-deleterious to performance or properties of the capsule. More particularly, any ethanol that is present must be below a threshold concentration at which integrity of the capsule shell is compromised. Typically the encapsulated liquid comprises zero to less than about 5% by weight ethanol. This is especially important where a hard capsule shell, for example a hard gelatin or hydroxypropylmethylcellulose (HPMC) capsule shell, is used. Soft capsule shells, for example soft gelatin or starch-based shells containing a plasticizer, can tolerate somewhat higher amounts of ethanol. Certain pre-blended phospholipid products useful herein contain small amounts of ethanol that are non-deleterious even to a hard gelatin capsule; for example Phosal 53 MCT™ can contain up to about 6% ethanol. When used illustratively in an amount not exceeding about 75% by weight of the encapsulated liquid, Phosal 53 MCT™ is seen to contribute ethanol in an amount not exceeding about 4.5% by weight of the encapsulated liquid, which remains "substantially non-ethanolic" as defined herein.

In most embodiments, the encapsulated liquid is also "substantially non-aqueous", i.e., having no water, or having an amount of water that is small enough to be, in practical terms, essentially non-deleterious to performance or properties of the composition. Typically, the encapsulated liquid comprises zero to less than about 5% by weight water. It will be understood that certain ingredients useful herein can bind small amounts of water on or within their molecules or supramolecular structures; such bound water if present does not affect the "substantially non-aqueous" character of the carrier as defined herein. Furthermore, according to those embodiments where a poorly lipid-soluble antioxidant is used, a small amount of water, generally not exceeding about 1% by weight of the encapsulated liquid, is generally necessary.

As indicated above, the encapsulated liquid comprises, inter alia, a phospholipid, and a pharmaceutically acceptable solubilizing agent for the phospholipid. It will be understood that reference in the singular to a (or the) phospholipid, solubilizing agent or other formulation ingredient herein includes the plural; thus combinations, for example mixtures, of more than one phospholipid, or more than one solubilizing agent, are expressly contemplated herein. The solubilizing agent, or the combination of solubilizing agent and phospholipid, may also assist in solubilizing the ABT-263, as may other ingredients, such as a non-phospholipid surfactant.

Any pharmaceutically acceptable phospholipid or mixture of phospholipids can be used. In general such phospholipids are phosphoric acid esters that yield on hydrolysis phosphoric acid, fatty acid(s), an alcohol and a nitrogenous base. Pharmaceutically acceptable phospholipids can include without limitation phosphatidylcholines, phosphatidylserines and phosphatidylethanolamines. In one embodiment the composition comprises phosphatidylcholine, derived for example from natural lecithin. Any source of lecithin can be used, including animal sources such as egg yolk, but plant sources are generally preferred. Soy is a particularly rich source of lecithin that can provide phosphatidylcholine for use in the present invention.

Illustratively, a suitable amount of phospholipid is about 15% to about 60%, for example about 20% to about 45%, by weight of the encapsulated liquid, although greater and lesser amounts can be useful in particular situations.

Ingredients useful as components of the solubilizing agent include glycols, glycolides and glycerides.

Glycols are generally suitable only where a soft capsule shell is to be used, and tend to be incompatible with hard shells such as hard gelatin shells. Suitable glycols for soft capsules of the invention include propylene glycol and polyethylene glycols (PEGs) having molecular weight of about 200 to about 1,000 g/mol, e.g., PEG 400, which has an average molecular weight of about 400 g/mol. Such glycols can provide relatively high solubility of ABT-263; however in some cases ABT-263 can exhibit chemical degradation, for example sulfoxide formation, to some degree when in solution in presence of such glycols. This can be evident by color changes of the solution with time. The higher the glycol content of the carrier, the greater may be the tendency for degradation of the ABT-263. In one embodiment, therefore, one or more glycols are present in a total glycol amount of at least about 1% but less than about 50%, for example less than about 30%, less than about 20%, less than about 15% or less than about 10% by weight of the encapsulated liquid. In another embodiment, the carrier comprises substantially no glycol.

Glycolides are glycols such as propylene glycol or PEG esterified with one or more organic acids, for example medium- to long-chain fatty acids. Suitable examples include propylene glycol monocaprylate, propylene glycol monolaurate and propylene glycol dilaurate products such as, for example. Capmul PG-8™, Capmul PG-12™ and Capmul PG-2L™ respectively of Abitec Corp. and products substantially equivalent thereto.

Suitable glycerides include, without limitation, medium- to long-chain mono-, di- and triglycerides. The term "medium-chain" herein refers to hydrocarbyl chains individually having more than about 6 and less than about 12 carbon atoms, including for example $C_8$ to $C_{10}$ chains. Thus glyceride materials comprising caprylyl and capryl chains, e.g., caprylic/capric mono-, di- and/or triglycerides, are examples of "medium-chain" glyceride materials herein. The term "long-chain" herein refers to hydrocarbyl chains individually having at least about 12, for example about 12 to about 18, carbon atoms, including for example lauryl, myristyl, cetyl, stearyl, oleyl, linoleyl and linolenyl chains. Medium- to long-chain hydrocarbyl groups in the glyceride materials can be saturated, mono- or polyunsaturated.

In one embodiment the encapsulated liquid comprises, as a major component of the solubilizing agent, one or more medium-chain triglycerides. A suitable example of a medium-chain triglyceride material is a caprylic/capric triglyceride product such as, for example, Captex 355 EP™ of Abitec Corp. and products substantially equivalent thereto. Optionally, as a further major component of the solubilizing agent of this embodiment, the encapsulated liquid further comprises one or more medium-chain mono- and/or diglycerides. A suitable example of such a component is a caprylic/capric mono- and diglyceride product such as, for example, Imwitor 742™ of Sasol Germany GmbH and products substantially equivalent thereto.

Where one or more glycerides are present as a major component of the solubilizing agent, a suitable total amount of glycerides is an amount effective to solubilize the phospholipid and, in combination with other excipients, effective to maintain ABT-263 in solution. For example, glycerides such as medium-chain mono-, di- and triglycerides can be present in a total glyceride amount of about 15% to about 60%, for example about 20% to about 45%, by weight of the encapsulated liquid, although greater and lesser amounts can be useful in particular situations. In one embodiment, the encapsulated liquid comprises about 7% to about 30%, for example about 10% to about 25%, by weight medium-chain triglycerides and about 7% to about 30%, for example about 10% to about 25%, by weight medium-chain mono- and diglycerides.

Conveniently, pre-blended products are available containing a suitable phospholipid/solubilizing agent combination for use in compositions of the present invention. It is emphasized that, while compositions comprising such products are embraced by the present invention, no limitation to such compositions is intended. Pre-blended phospholipid/solubilizing agent products can be advantageous in improving ease of preparation of the present compositions.

An illustrative example of a pre-blended phospholipid+solubilizing agent product is Phosal 53 MCT™, available from Phospholipid GmbH, which contains, by weight, not less than 53% phosphatidylcholine, not more than 6% lysophosphatidylcholine, about 29% medium-chain triglycerides, 3-6% (typically about 5%) ethanol, about 3% mono- and diglycerides from sunflower oil, about 2% oleic acid, and about 0.2% ascorbyl palmitate.

Another illustrative example is Lipoid S75™, available from Lipoid GmbH, which contains, by weight, not less than 70% phosphatidylcholine in a solubilizing system. This can be further blended with medium-chain triglycerides, for example in a 30/70 weight/weight mixture, to provide a product ("Lipoid S75™ MCT") containing, by weight, not less than 20% phosphatiylcholine, 2-4% phosphatidylethanolamine, not more than 1.5% lysophosphatidyl-choline, and 67-73% medium-chain triglycerides.

Yet another illustrative example of a pre-blended phospholipid+solubilizing agent product, in this case suitable only for soft capsules of the invention, is Phosal 50 PG™, available from Phospholipid GmbH, which comprises, by weight, not less than 50% phosphatidylcholine, not more than 6% lysophosphatidylcholine, about 35% propylene glycol, about 3% mono- and diglycerides from sunflower oil, about 2% soy fatty acids, about 2% ethanol, and about 0.2% ascorbyl palmitate.

The phosphatidylcholine component of each of these pre-blended products is derived from soy lecithin. Products having substantially equivalent composition may be obtainable from other suppliers. A product having "substantially equivalent composition" in the present context means having a composition sufficiently similar to the reference composition in its ingredient list and relative amounts of ingredients to exhibit no practical difference in properties with respect to utilization of the product herein.

The encapsulated liquid further comprises a pharmaceutically acceptable non-phospholipid surfactant. One of skill in the art will be able to select a suitable surfactant for use in a capsule of the invention, based on information herein. Such a surfactant can serve various functions, including for example enhancing dispersion of the encapsulated liquid upon release from the capsule in the aqueous environment of the gastrointestinal tract. Thus in one embodiment the non-phospholipid surfactant is a dispersing and/or emulsifying agent that enhances dispersion and/or emulsification of the capsule contents in real or simulated gastrointestinal fluid. Illustratively, a surfactant such as a polysorbate (polyoxyethylene sorbitan ester), e.g., polysorbate 80 (available for example as Tween™ 80 from Uniqema), can be included in an amount of about 7% to about 30%, for example about 10% to about 25%, by weight of the encapsulated liquid.

ABT-263 is susceptible to degradation, including by formation of sulfoxides, in an oxidative environment; thus it is desirable to include an antioxidant in the composition. Antioxidants used in pharmaceutical compositions are most typically agents that inhibit generation of oxidative species such as triplet or singlet oxygen, superoxides, peroxide and free hydroxyl radicals, or agents that scavenge such oxidative species as they are generated. Examples of commonly used antioxidants of these classes include butylated hydroxyanisole (BHA), butylated hydroxytoluene (BHT), retinyl palmitate, tocopherol, propyl gallate, ascorbic acid and ascorbyl palmitate. The present inventors have found, however, that at least some commonly used antioxidants are ineffective to protect ABT-263 from excessive sulfoxide formation in encapsulated liquid formulations as described herein.

For example, BHA, added at 0.2% by weight to a 15% by weight solution of ABT-263 free base in a medium referred to herein as "IPT-253" (20% Imwitor 742™, 50% Phosal 53 MCT™, 30% Tween™ 80), has been found to have no effect on sulfoxide formation in a 4-week stability study at 40° C. without nitrogen purging of headspace, as shown in Table 3. A full report of this study is found in Example 7 herein.

TABLE 3

Effect of 0.2% BHA on ABT-263 sulfoxide formation in IPT-253 solution

| Time (weeks) | % Total sulfoxides | |
|---|---|---|
| | No antioxidant | 0.2% BHA |
| 0 | not detectable | 0.06 |
| 1 | 0.26 | 0.29 |
| 2 | 0.47 | 0.49 |
| 3 | 0.56 | 0.58 |
| 4 | 0.67 | 0.68 |

Antioxidants that, by contrast, have been found effective are sulfur-containing compounds, including compounds of formula

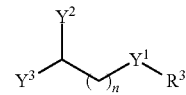

where
n is 0, 1 or 2;
$Y^1$ is S;
$Y^2$ is $NHR^1$, OH or H, where $R^1$ is alkyl or alkylcarbonyl;
$Y^3$ is $COOR^2$ or $CH_2OH$, where $R^2$ is H or alkyl; and
$R^3$ is H or alkyl;
where alkyl groups are independently optionally substituted with one of more substituents independently selected from the group consisting of carboxyl, alkylcarbonyl, alkoxycarbonyl, amino and alkylcarbonylamino; a pharmaceutically acceptable salt thereof; or, where $Y^1$ is S and $R^3$ is H, an —S—S— dimer thereof or pharmaceutically acceptable salt of such dimer; or compounds of formula

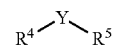

where
Y is S or S—S; and
$R^4$ and $R^5$ are independently selected from H, alkyl and $(CH_2)_nR^6$ where n is 0-10 and $R^6$ is arylcarbonyl, alkylcarbonyl, alkoxycarbonyl, carboxyl or $CHR^7R^8$-substituted alkyl, where $R^7$ and $R^8$ are independently $CO_2R^9$, $CH_2OH$, hydrogen or $NHR^{10}$, where $R^9$ is H, alkyl, substituted alkyl or arylalkyl and $R^{10}$ is hydrogen, alkyl, alkylcarbonyl or alkoxycarbonyl.

An "alkyl" substituent or an "alkyl" or "alkoxy" group forming part of a substituent is one having 1 to about 18 carbon atoms and can consist of a straight or branched chain. An "aryl" group forming part of a substituent is a phenyl group, unsubstituted or substituted with one or more hydroxy, alkoxy or alkyl groups.

$R^1$ is illustratively $C_{1-4}$ alkyl (e.g., methyl or ethyl) or ($C_{1-4}$ alkyl)carbonyl (e.g., acetyl).

$R^2$ is illustratively H or $C_{1-18}$ alkyl, for example methyl, ethyl, propyl (e.g., n-propyl or isopropyl), butyl (e.g., n-butyl, isobutyl or t-butyl), octyl (e.g., n-octyl or 2-ethylhexyl), dodecyl (e.g., lauryl), tridecyl, tetradecyl, hexadecyl or octadecyl (e.g., stearyl).

$R^3$ is typically H or $C_{1-4}$ alkyl (e.g., methyl or ethyl).

A sulfur-containing antioxidant of either of the above formulae can be, for example, a natural or synthetic amino acid or a derivative thereof such as an alkyl ester or N-acyl derivative, or a salt of such amino acid or derivative. Where the amino acid or derivative thereof is derived from a natural source it is typically in the L-configuration; however it is understood that D-isomers and D,L-isomer mixtures can be substituted if necessary.

Non-limiting examples of such sulfur-containing compounds useful herein include β-alkylmercaptoketones, cysteine, cystine, homocysteine, methionine, thiodiglycolic acid, thiodipropionic acid, thioglycerol and salts, esters, amides and thioethers thereof; and combinations thereof. More particularly, one or more of such compounds can be selected from N-acetylcysteine, N-acetylcysteine butyl ester, N-acetylcysteine dodecyl ester, N-acetyl-cysteine ethyl ester, N-acetylcysteine methyl ester, N-acetylcysteine octyl ester, N-acetyl-cysteine propyl ester, N-acetylcysteine stearyl ester, N-acetylcysteine tetradecyl ester, N-acetylcysteine tridecyl ester, N-acetylmethionine, N-acetylmethionine butyl ester, N-acetyl-methionine dodecyl ester, N-acetylmethionine ethyl ester, N-acetylmethionine methyl ester, N-acetylmethionine octyl ester, N-acetylmethionine propyl ester, N-acetylmethionine stearyl ester, N-acetylmethionine tetradecyl ester, N-acetylmethionine tridecyl ester, cysteine, cysteine butyl ester, cysteine dodecyl ester, cysteine ethyl ester, cysteine methyl ester, cysteine octyl ester, cysteine propyl ester, cysteine stearyl ester, cysteine tetradecyl ester, cysteine tridecyl ester, cystine, cystine dibutyl ester, cystine di(dodecyl) ester, cystine diethyl ester, cystine dimethyl ester, cystine dioctyl ester, cystine dipropyl ester, cystine distearyl ester, cystine di(tetradecyl) ester, cystine di(tridecyl) ester, N,N-diacetylcystine, N,N-diacetylcystine dibutyl ester, N,N-diacetylcystine diethyl ester, N,N-diacetylcystine di(dodecyl) ester, N,N-diacetylcystine dimethyl ester, N,N-diacetylcystine dioctyl ester, N,N-diacetylcystine dipropyl ester, N,N-diacetylcystine distearyl ester, N,N-diacetylcystine di(tetradecyl) ester, N,N-diacetylcystine di(tridecyl) ester, dibutyl thiodiglycolate, dibutyl thiodipropionate, di(dodecyl) thiodiglycolate, di(dodecyl) thiodipropionate, diethyl thiodiglycolate, diethyl thiodipropionate, dimethyl thiodiglycolate, dimethyl thiodipropionate, dioctyl thiodiglycolate, dioctyl thiodipropionate, dipropyl thiodiglycolate, dipropyl thiodipropionate, distearyl thiodiglycolate, distearyl thiodipropionate, di(tetradecyl) thiodiglycolate, di(tetradecyl) thiodipropionate, homocysteine, homocysteine butyl ester, homocysteine dodecyl ester, homocysteine ethyl ester, homocysteine methyl ester, homocysteine octyl ester, homocysteine propyl ester, homocysteine stearyl ester, homocysteine tetradecyl ester, homocysteine tridecyl ester, methionine, methionine butyl ester, methionine dodecyl ester, methionine ethyl ester, methionine methyl ester, methionine octyl ester, methionine propyl ester, methionine stearyl ester, methionine tetradecyl ester, methionine tridecyl ester, S-methylcysteine, S-methylcysteine butyl ester, S-methylcysteine dodecyl ester, S-methylcysteine ethyl ester, S-methylcysteine methyl ester, S-methylcysteine octyl ester, S-methylcysteine propyl ester, S-methylcysteine stearyl ester, S-methylcysteine tetradecyl ester, S-methylcysteine tridecyl ester, thiodiglycolic acid, thiodipropionic acid, thioglycerol, isomers and mixtures of isomers thereof, and salts thereof.

Salts of the above compounds can be acid addition salts such as the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetate, trifluoroacetate, para-toluenesulfonate and undecanoate salts.

Without being bound by theory, it is generally believed that sulfur-containing antioxidants such as those exemplified above protect the ABT-263 by being themselves more readily oxidizable and, therefore, being oxidized preferentially over the ABT-263. In general, for this mode of operation to provide an acceptable degree of protection for the ABT-263, the antioxidant must be present in a substantial amount, for example in a molar ratio to ABT-263 of at least about 1:10. In some embodiments, the molar ratio of antioxidant to ABT-263 is about 1:10 to about 2:1, for example about 1:5 to about 1.5:1. Best results will sometimes be obtained when the molar ratio is approximately 1:1, i.e., about 8:10 to about 10:8.

Notwithstanding the antioxidant efficacy of sulfur-containing antioxidants of the above formulae, the present inventors have found that, at molar ratios of approximately 1:1, such antioxidants have a tendency to result in solutions that become cloudy upon storage, when ABT-263 is used in the form of its free base. For solutions containing ABT-263 in the form of its bis-HCl salt, this tendency is absent or at least less marked.

However, in yet another unexpected discovery, ABT-263 free base has been found to be less susceptible to sulfoxide formation than ABT-263 bis-HCl when formulated in lipid solution (but in the absence of antioxidant), as shown in Table 6 (see Example 3 hereinbelow). The solvent system in solution A is Phosal 53 MCT™/ethanol, 9:1 v/v; and in solution B is Labrafil M 1944 CS™/oleic acid/polysorbate 80, 30%/40%/30% by weight. (Labrafil M 1944 CS™ of Gattefossé contains polyoxyethylene glyceryl monooleate.) The three-week study was conducted at 40° C. without nitrogen purging of headspace.

To take advantage of the unexpected finding that ABT-263 is less susceptible to sulfoxide formation in its free-base than salt form, the present inventors have turned to a different class of sulfur-containing antioxidants, namely inorganic antioxidants of the sulfite, bisulfite, metabisulfite and thiosulfate classes. To complicate matters, these antioxidants are poorly lipid-soluble and must be introduced to the solution for encapsulation in aqueous solution. Presence of water promotes sulfoxide formation in ABT-263 solutions, the very effect that is sought to be minimized. To restrict the amount of added water, poorly lipid-soluble antioxidants are, in one embodiment of the present invention, added at much lower concentrations than those providing molar equivalence to the concentration of ABT-263.

Where a poorly lipid-soluble antioxidant such as a sulfite, bisulfite, metabisulfite or thiosulfate antioxidant is used, it is accompanied in the solution for encapsulation by water in an amount not exceeding about 1% by weight, for example about 0.2% to about 0.8% by weight. The amount of such antioxidant that can be introduced in such a small amount of water typically does not exceed about 0.2% by weight, and is for example an amount of about 0.02% to about 0.2%, or about 0.05% to about 0.15%, by weight, of the solution for encapsulation.

To minimize the amount of water added to the formulation, it is desirable to provide the antioxidant in the form of a relatively concentrated aqueous stock solution, for example having at least about 10% by weight antioxidant. However, it has been found that where an excessively concentrated stock solution (e.g., about 20% or higher) is used, this can result in undesirable precipitation of solids in the formulation. Suitable concentrations of antioxidant in the stock solution are typically about 10% to about 18%, illustratively about 15%, by weight.

Sodium and potassium salts of sulfites, bisulfites, metabisulfites and thiosulfates are useful antioxidants according to the present embodiment; more particularly sodium and potassium metabisulfites.

Optionally, a composition of the present invention further comprises a chelating agent. In some circumstances, a chelating agent such as ethylenediaminetetraacetic acid (EDTA or edetate), carvedilol, citric acid and salts thereof, choline citrate, tartaric acid and salts thereof and the like can further improve storage stability of the formulation. It is believed, without being bound by theory, that a chelating agent can enhance antioxidant effectiveness by sequestering metal ions that catalyze or otherwise promote oxidative degradation of the drug compound.

In one embodiment, EDTA or a salt thereof (e.g., disodium EDTA or calcium disodium EDTA) is optionally added, for example in an amount of about 0.002% to about 0.02% by weight of the solution for encapsulation. EDTA can be added as an aqueous stock solution in the same manner as the antioxidant. The antioxidant and EDTA can, if desired, be added as components of the same stock solution.

Surprisingly at the very low concentrations of poorly lipid-soluble antioxidant such as sodium metabisulfite contemplated herein (typically the molar ratio of such antioxidant to ABT-263 according to the present embodiment is no greater than about 1:20), sulfoxide formation has been found to remain within acceptable limits, as illustrated in Example 12 herein.

Sulfoxide formation can be further minimized by selecting formulation ingredients having low peroxide value. Peroxide value is a well established property of pharmaceutical excipients and is generally expressed (as herein) in units corresponding to milliequivalents of peroxides per kilogram of excipient (meq/kg). Some excipients inherently have low peroxide value, but others, for example those having unsaturated fatty acid such as oleyl moieties and/or polyoxyethylene chains, can be sources of peroxides. In the case of polysorbate 80, for example, it is preferable to select a source of polysorbate 80 having a peroxide value not greater than about 5, for example not greater than about 2. Suitable sources include Crillet 4HP™ and Super-Refined Tween 80™, both available from Croda.

Illustratively, the encapsulated liquid solution according to the present embodiment comprises:
about 5% to about 20% by weight ABT-263 free base,
about 15% to about 60% by weight phosphatidylcholine,
about 7% to about 30% by weight of medium-chain triglycerides,
about 7% to about 30% by weight of medium-chain mono- and diglycerides,
about 7% to about 30% polysorbate 80 surfactant,
about 0.02% to about 0.2% by weight sodium or potassium metabisulfite,
about 0.003% to about 0.01% EDTA or salt thereof, and
about 0.2% to about 0.8% water.

Other excipients can optionally be present in the encapsulated solution, so long as they do not adversely affect the storage stability, safety or therapeutic efficacy of the capsule to an unacceptable degree. However, in a more particular embodiment, the encapsulated liquid solution consists essentially of the ingredients listed immediately above.

The capsule shell can be of any pharmaceutically acceptable material, including hard or soft gelatin. A capsule shell size is selected appropriate to the amount of liquid to be encapsulated. For example, a size 0 capsule shell can be used to encapsulate up to about 600 mg of liquid and a size 00 capsule shell up to about 900 mg of liquid.

A prototype capsule of the present invention comprises a size 0 hard gelatin capsule shell having encapsulated therewithin a liquid solution that comprises:
about 50 mg ABT-263 free base,
about 150 mg phosphatidylcholine,
about 75 mg medium-chain triglycerides,
about 90 mg medium-chain mono- and diglycerides,
about 90 mg polysorbate 80 surfactant,
about 0.25 mg sodium or potassium metabisulfite,
about 0.025 mg EDTA or salt thereof, and
about 2.5 mg water.

The term "about" in the immediately preceding description of a prototype capsule will be understood to mean that the amounts shown can vary within usual manufacturing tolerances accepted in the pharmaceutical industry.

The constraints of chemical and physical stability leading to the capsule of the present invention can present a still further challenge with respect to bioavailability when administered orally. Acceptable bioavailability can be evidenced, for example, by pharmacokinetic (PK) parameters including peak plasma concentration ($C_{max}$) and area under the plasma concentration-time curve (AUC), calculated from zero to 24 hours from time of administration ($AUC_{0-24}$) or from zero to infinity ($AUC_{0-\infty}$). Illustratively, bioavailability can be expressed as a percentage, for example using the parameter F, which computes AUC for oral delivery of a test composition as a percentage of AUC for intravenous (i.v.) delivery of the drug in a suitable solvent, taking into account any difference between oral and i.v. doses.

Bioavailability can be determined by PK studies in humans or in any suitable model species. For present purposes, a dog model, as illustratively described in Example 11 below, is generally suitable. In various illustrative embodiments, capsules of the invention exhibit oral ABT-263 bioavailability of at least about 30%, at least about 35% or at least about 40%, up to or exceeding about 50%, in a dog model, when administered as a single ABT-263 dose of about 2.5 to about 10 mg/kg to fasting or non-fasting animals.

In one example, the capsule comprises ABT-263 in free-base or salt form and excipients selected to provide (a) solubility of ABT-263 of at least about 40 mg/g, for example at least about 50 mg/g, at least about 60 mg/g, at least about 70 mg/g, at least about 80 mg/g or at least about 100 mg/g, at about 25° C.; and (b) a PK profile upon oral administration of the composition in a dog model exhibiting a bioavailability of at least about 30%.

In a particular embodiment, the capsule is a prototype capsule as described above or another capsule of the present invention that is substantially bioequivalent thereto.

The term "substantially bioequivalent" herein means exhibiting, in a human PK single- or multiple-dose study in fasting or non-fasting conditions, substantially equal $C_{max}$ and substantially equal exposure measured as AUC, for example $AUC_{0-24}$ or $AUC_{0-\infty}$. The compositions being compared for substantial bioequivalence should be administered at the same dose or doses, expressed in the case of ABT-263 as free-base equivalent. If a multiple-dose study is used to draw the comparison, it is the steady-state values of $C_{max}$ and AUC that are used. In the present context, $C_{max}$ or AUC of a test composition is "substantially equal" if it is no less than 80% and no greater than 125% of the corresponding parameter in a reference composition (e.g., the prototype capsule described above).

The present invention is not limited by the process used to prepare a capsule as embraced or described herein. Any suitable process of pharmacy can be used. Illustratively, a capsule of the invention can be prepared by a process comprising simple mixing of the recited ingredients, wherein order of addition is not critical, to form a liquid solution for encapsulation, followed by encapsulation of the liquid in a capsule shell, for example a hard or soft gelatin capsule shell, to form a capsule. It is noted, however, that if the phospholipid is used in its solid state, for example in the form of soy lecithin, it will generally be desirable to first solubilize the phospholipid with the solubilizing agent or part thereof. Thereafter other excipients and the ABT-263 can be added by simple mixing, with agitation as appropriate. Use of a pre-blended product comprising phospholipid and solubilizing agent can simplify preparation of the composition. For example, the phospholipid can comprise phosphatidylcholine and the solubilizing agent pre-blended therewith can comprise medium-chain triglycerides, as in the case of Phosal 53 MCT™ or Lipoid S75™ MCT. Illustratively, the pre-blended product comprises about 50% to about 75% phosphatidylcholine and about 15% to about 30% medium-chain triglycerides.

Where the solution for encapsulation comprises a poorly lipid-soluble sulfur-containing antioxidant such as sodium or potassium metabisulfite, the process should be adjusted. An illustrative process for preparing a capsule containing such a solution comprises the following steps.

An API (active pharmaceutical ingredient) that consists essentially of ABT-263 free base or a pharmaceutically acceptable salt thereof (e.g., ABT-263 bis-HCl) is dissolved in a medium comprising the phospholipid and at least a portion of the solubilizing agent to provide a lipid solution of ABT-263. As noted above, a pre-blended product comprising the phospholipid and solubilizing agent can be used as the medium for dissolution of the API.

Where ABT-263 is to be formulated in its free-base form, any solid-state form of ABT-263 free base can serve as the API. However, it will generally be found preferable to use a crystalline form of ABT-263 free base as API, for example a solvated or non-solvated crystalline form. In a particular embodiment of the present method, a non-solvated crystalline form such as Form I or Form II crystalline ABT-263 as described herein is used as API.

The non-phospholipid surfactant and, optionally, the balance of the solubilizing agent, is admixed with the solubilizing agent (prior to or simultaneously with dissolution of the API) or with the lipid solution (after dissolution of the API). As noted above, the non-phospholipid surfactant is illustratively a polysorbate such as polysorbate 80. The balance of the solubilizing agent can be the same material as the portion of solubilizing agent used together with the phospholipid to dissolve the ABT-263; alternatively it can be a different material. For example, the portion of solubilizing agent used together with the phospholipid for dissolution of the ABT-263 can comprise one or more medium-chain triglycerides, and the balance of solubilizing agent admixed in the present step can comprise one or more medium-chain mono- and/or diglycerides, for example a caprylic/capric mono- and diglyceride product such as Imwitor 742™.

Separately, the poorly lipid-soluble sulfur-containing antioxidant is dissolved in water to prepare an aqueous stock solution. Stock solutions at about 10% to about 18% by weight concentration will generally be found suitable, as explained above.

The aqueous stock solution is then admixed with the lipid solution, typically after addition of the non-phospholipid surfactant, to provide a liquid solution for encapsulation.

In a final step, the resulting liquid solution is encapsulated in a capsule shell by any known encapsulation process.

Compositions embraced herein, including compositions described generally or with specificity herein, are useful for orally delivering ABT-263 to a subject. Accordingly, a method of the invention for delivering ABT-263 to a subject comprises orally administering one to a plurality of capsules as described above.

The subject can be human or non-human (e.g., a farm, zoo, work or companion animal, or a laboratory animal used as a model) but in an important embodiment the subject is a human patient in need of the drug, for example to treat a disease characterized by apoptotic dysfunction and/or over-expression of an anti-apoptotic Bcl-2 family protein. A human subject can be male or female and of any age, but is typically an adult.

The composition is normally administered in an amount providing a therapeutically effective daily dose of ABT-263. The term "daily dose" herein means the amount of drug administered per day, regardless of the frequency of administration. For example, if the subject receives a unit dose of 150 mg twice daily, the daily dose is 300 mg. Use of the term "daily dose" will be understood not to imply that the specified dosage amount is necessarily administered once daily. However, in a particular embodiment the dosing frequency is once daily (q.d.), and the daily dose and unit dose are in this embodiment the same thing.

What constitutes a therapeutically effective dose depends on the subject (including species and body weight of the subject), the disease (e.g., the particular type of cancer) to be treated, the stage and/or severity of the disease, the individual subject's tolerance of the drug, whether the drug is administered in monotherapy or in combination with one or more other drugs, e.g., other chemotherapeutics for treatment of cancer, and other factors. Thus the daily dose of ABT-263 can vary within wide margins, for example from about 10 to about 1,000 mg. Greater or lesser daily doses can be appropriate in specific situations. It will be understood that recitation herein of a "therapeutically effective" dose herein does not necessarily require that the drug be therapeutically effective if only a single such dose is administered; typically therapeutic efficacy depends on the composition being administered repeatedly according to a regimen involving appropriate frequency and duration of administration. It is strongly preferred that, while the daily dose selected is sufficient to provide benefit in terms of treating the cancer, it should not be sufficient to provoke an adverse side-effect to an unacceptable or intolerable degree. A suitable therapeutically effective dose can be selected by the physician of ordinary skill without undue experimentation based on the disclosure herein and on art cited herein, taking into account factors such as those mentioned above. The physician may, for example, start a cancer patient on a course of therapy with a relatively low daily dose and titrate the dose upwards over a period of days or weeks, to reduce risk of adverse side-effects.

Illustratively, suitable doses of ABT-263 are generally about 25 to about 1,000 mg/day, more typically about 50 to about 500 mg/day or about 200 to about 400 mg/day, for example about 50, about 100, about 150, about 200, about 250, about 300, about 350, about 400, about 450 or about 500 mg/day, administered at an average dosage interval of about 3 hours to about 7 days, for example about 8 hours to about 3 days, or about 12 hours to about 2 days. In most cases a once-daily (q.d.) administration regimen is suitable.

An "average dosage interval" herein is defined as a span of time, for example one day or one week, divided by the number of unit doses administered over that span of time. For example, where a drug is administered three times a day, around 8 am, around noon and around 6 pm, the average dosage interval is 8 hours (a 24-hour time span divided by 3). A single capsule or a plurality (e.g., 2 to about 10) of capsules administered at one time is considered a unit dose for the purpose of defining the average dosage interval.

A daily dosage amount and dosage interval can, in some embodiments, be selected to maintain a plasma concentration of ABT-263 in a range of about 0.5 to about 10 µg/ml. Thus, during a course of ABT-263 therapy according to such embodiments, the steady-state peak plasma concentration ($C_{max}$) should in general not exceed about 10 µg/ml, and the steady-state trough plasma concentration ($C_{min}$) should in general not fall below about 0.5 µg/ml. It will further be found desirable to select, within the ranges provided above, a daily dosage amount and average dosage interval effective to provide a $C_{max}/C_{min}$ ratio not greater than about 5, for example not greater than about 3, at steady-state. It will be understood that longer dosage intervals will tend to result in greater $C_{max}/C_{min}$ ratios. Illustratively, at steady-state, an ABT-263 $C_{max}$ of about 3 to about 8 µg/ml and $C_{min}$ of about 1 to about 5 µg/ml can be targeted by the present method. Steady-state values of $C_{max}$ and $C_{min}$ can be established in a human PK study, for example conducted according to standard protocols including but not limited to those acceptable to a regulatory agency such as the U.S. Food and Drug Administration (FDA).

One to a plurality of capsules can be swallowed whole, typically with the aid of water or other imbibable liquid to help the swallowing process.

As compositions of the present invention typically exhibit only a minor food effect, administration according to the present embodiment can be with or without food, i.e., in a non-fasting or fasting condition. It is generally preferred to administer the present compositions to a non-fasting patient.

Without being bound by theory, it is believed that the therapeutic efficacy of ABT-263 is due at least in part to its ability to bind to a Bcl-2 family protein such as Bcl-2, Bcl-$X_L$ or Bcl-w in a way that inhibits the anti-apoptotic action of the protein, for example by occupying the BH3 binding groove of the protein.

In still further embodiments of the invention, there is provided a method for treating a disease characterized by apoptotic dysfunction and/or overexpression of an anti-apoptotic Bcl-2 family protein, comprising administering to a subject having the disease a therapeutically effective amount of ABT-263 formulated in a liquid-filled capsule as described herein.

Capsule formulations of the present invention are suitable for use in monotherapy or in combination therapy, for example with other chemotherapeutics or with ionizing radiation. A particular advantage of the present invention is that it permits once-daily oral administration, a regimen which is convenient for the patient who is undergoing treatment with other orally administered drugs on a once-daily regimen. Oral administration is easily accomplished by the patient him/herself or by a caregiver in the patient's home; it is also a convenient route of administration for patients in a hospital or residential care setting.

Combination therapies illustratively include administration of the present ABT-263 composition concomitantly with one or more of bortezomid, carboplatin, cisplatin, cyclophosphamide, dacarbazine, dexamethasone, docetaxel, doxorubicin, etoposide, fludarabine, hydroxydoxorubicin, irinotecan, paclitaxel, rapamycin, rituximab, vincristine and the like, for example with a polytherapy such as CHOP (cyclophosphamide+hydroxydoxorubicin+vincristine+prednisone), RCVP (rituximab+cyclophosphamide+vincristine+prednisone), R-CHOP (rituximab+CHOP) or DA-EPOCH-R (dose-adjusted etoposide, prednisone, vincristine, cyclophosphamide, doxorubicin and rituximab).

An ABT-263 composition can be administered in combination therapy with one or more therapeutic agents that include, but are not limited to, angiogenesis inhibitors, antiproliferative agents, other apoptosis promoters (for example, Bcl-xL, Bcl-w and Bfl-1 inhibitors), activators of a death receptor pathway, BiTE (bi-specific T-cell engager) antibodies, dual variable domain binding proteins (DVDs), inhibitors of apoptosis proteins (IAPB), microRNAs, mitogen-activated extracellular signal-regulated kinase inhibitors, multivalent binding proteins, poly-ADP (adenosine diphosphate)-ribose polymerase (PARP) inhibitors, small inhibitory ribonucleic acids (siRNAs), kinase inhibitors, receptor tyrosine kinase inhibitors, aurora kinase inhibitors, polo-like kinase inhibitors, bcr-abl kinase inhibitors, growth factor inhibitors, COX-2 inhibitors, non-steroidal anti-inflammatory drugs (NSAIDs), antimitotic agents, alkylating agents, antimetabolites, intercalating antibiotics, platinum-containing chemotherapeutic agents, growth factor inhibitors, ionizing radiation, cell cycle inhibitors, enzymes, topoisomerase inhibitors, biologic response modifiers, immunologicals, antibodies, hormonal therapies, retinoids, deltoids, plant alkaloids, proteasome inhibitors, HSP-90 inhibitors, histone deacetylase (HDAC) inhibitors, purine analogs, pyrimidine analogs, MEK inhibitors, CDK inhibitors, ErbB2 receptor inhibitors, mTOR inhibitors as well as other antitumor agents.

Angiogenesis inhibitors include, but are not limited to, EGFR inhibitors, PDGFR inhibitors, VEGFR inhibitors, TIE2 inhibitors, IGF1R inhibitors, matrix metalloproteinase 2 (MMP-2) inhibitors, matrix metalloproteinase 9 (MMP-9) inhibitors and thrombospondin analogs.

Examples of EGFR inhibitors include, but are not limited to, gefitinib, erlotinib, cetuximab, EMD-7200, ABX-EGF, HR3, IgA antibodies, TP-38 (IVAX), EGFR fusion protein, EGF-vaccine, anti-EGFR immunoliposomes and lapatinib.

Examples of PDGFR inhibitors include, but are not limited to, CP-673451 and CP-868596.

Examples of VEGFR inhibitors include, but are not limited to, bevacizumab, sunitinib, sorafenib, CP-547632, axitinib, vandetanib, AEE788, AZD-2171, VEGF trap, vatalanib, pegaptanib, IM862, pazopanib, ABT-869 and angiozyme.

Bcl-2 family protein inhibitors other than ABT-263 include, but are not limited to, AT-101 ((−)gossypol), Genasense™ Bcl-2-targeting antisense oligonucleotide (G3139 or oblimersen), IPI-194, IPI-565, ABT-737, GX-070 (obatoclax) and the like.

Activators of a death receptor pathway include, but are not limited to, TRAIL, antibodies or other agents that target death receptors (e.g., DR4 and DR5) such as apomab, conatumumab, ETR2-ST01, GDC0145 (lexatumumab), HGS-1029, LBY-135, PRO-1762 and trastuzumab.

Examples of thrombospondin analogs include, but are not limited to, TSP-1, ABT-510, ABT-567 and ABT-898.

Examples of aurora kinase inhibitors include, but are not limited to, VX-680, AZD-1152 and MLN-8054.

An example of a polo-like kinase inhibitor includes, but is not limited to, BI-2536.

Examples of bcr-abl kinase inhibitors include, but are not limited to, imatinib and dasatinib.

Examples of platinum-containing agents include, but are not limited to, cisplatin, carboplatin, eptaplatin, lobaplatin, nedaplatin, oxaliplatin and satraplatin.

Examples of mTOR inhibitors include, but are not limited to, CCI-779, rapamycin, temsirolimus, everolimus, RAD001 and AP-23573.

Examples of HSP-90 inhibitors include, but are not limited to, geldanamycin, radicicol, 17-AAG, KOS-953, 17-DMAG, CNF-101, CNF-1010, 17-AAG-nab, NCS-683664, efungumab, CNF-2024, PU3, PU24FC1, VER-49009, IPI-504, SNX-2112 and STA-9090.

Examples of HDAC inhibitors include, but are not limited to, suberoylanilide hydroxamic acid (SAHA), MS-275, valproic acid, TSA, LAQ-824, trapoxin and depsipeptide.

Examples of MEK inhibitors include, but are not limited to, PD-325901, ARRY-142886, ARRY-438162 and PD-98059.

Examples of CDK inhibitors include, but are not limited to, flavopyridol, MCS-5A, CVT-2584, seliciclib ZK-304709, PHA-690509, BMI-1040, GPC-286199, BMS-387032, PD-332991 and AZD-5438.

Examples of COX-2 inhibitors include, but are not limited to, celecoxib, parecoxib, deracoxib, ABT-963, etoricoxib, lumiracoxib, BMS-347070, RS 57067, NS-398, valdecoxib, rofecoxib, SD-8381, 4-methyl-2-(3,4-dimethylphenyl)-1-(4-sulfamoylphenyl-1H-pyrrole, T-614, JTE-522, S-2474, SVT-2016, CT-3 and SC-58125.

Examples of NSAIDs include, but are not limited to, salsalate, diflunisal, ibuprofen, ketoprofen, nabumetone, piroxicam, naproxen, diclofenac, indomethacin, sulindac, tolmetin, etodolac, ketorolac and oxaprozin.

Examples of ErbB2 receptor inhibitors include, but are not limited to, CP-724714, canertinib, trastuzumab, petuzumab, TAK-165, ionafamib, GW-282974, EKB-569, PI-166, dHER2, APC-8024, anti-HER/2neu bispecific antibody B7.her2IgG3 and HER2 trifunctional bispecific antibodies mAB AR-209 and mAB 2B-1.

Examples of alkylating agents include, but are not limited to, nitrogen mustard N-oxide, cyclophosphamide, ifosfamide, trofosfamide, chlorambucil, melphalan, busulfan, mitobronitol, carboquone, thiotepa, ranimustine, nimustine, Cloretazine™ (laromustine), AMD-473, altretamine, AP-5280, apaziquone, brostallicin, bendamustine, carmustine, estramustine, fotemustine, glufosfamide, KW-2170, mafosfamide, mitolactol, lomustine, treosulfan, dacarbazine and temozolomide.

Examples of antimetabolites include, but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, pemeterxed, gemcitabine, fludarabine, 5-azacitidine, capecitabine, cladribine, clofarabine, decitabine, eflornithine, ethenylcytidine, cytosine arabinoside, hydroxyurea, TS-1, melphalan, nelarabine, nolatrexed, disodium pemeterxed, pentostatin, peliterxol, raltitrexed, triapine, trimeterxate, vidarabine, mycophenolic acid, ocfosfate, pentostatin, tiazofurin, ribavirin, EICAR, hydroxyurea and deferoxamine.

Examples of antibiotics include, but are not limited to, intercalating antibiotics, aclarubicin, actinomycin D, amrubicin, annamycin, adriamycin, bleomycin, daunorubicin, doxorubicin (including liposomal doxorubicin), elsamitrucin, epirubicin, glarubicin, idarubicin, mitomycin C, nemorubicin, neocarzinostatin, peplomycin, pirarubicin, rebeccamycin, stimalamer, streptozocin, valrubicin, zinostatin and combinations thereof.

Examples of topoisomerase inhibiting agents include, but are not limited to, aclarubicin, amonafide, belotecan, camptothecin, 10-hydroxycamptothecin, 9-amino-camptothecin, amsacrine, dexrazoxane, diflomotecan, irinotecan HCl, edotecarin, epirubicin, etoposide, exatecan, becatecarin, gimatecan, lurtotecan, orathecin, BN-80915, mitoxantrone, pirarubicin, pixantrone, rubitecan, sobuzoxane, SN-38, tafluposide and topotecan.

Examples of antibodies include, but are not limited to, rituximab, cetuximab, bevacizumab, trastuzumab, CD40-specific antibodies and IGF1R-specific antibodies, chTNT-1/B, denosumab, edrecolomab, WX G250, zanolimumab, lintuzumab and ticilimumab.

Examples of hormonal therapies include, but are not limited to, sevelamer carbonate, rilostane, luteinizing hormone releasing hormone, modrastane, exemestane, leuprolide acetate, buserelin, cetrorelix, deslorelin, histrelin, anastrozole, fosrelin, goserelin, degarelix, doxercalciferol, fadrozole, formestane, tamoxifen, arzoxifene, bicalutamide, abarelix, triptorelin, finasteride, fulvestrant, toremifene, raloxifene, trilostane, lasofoxifene, letrozole, flutamide, megesterol, mifepristone, nilutamide, dexamethasone, prednisone and other glucocorticoids.

Examples of retinoids or deltoids include, but are not limited to, seocalcitol, lexacalcitol, fenretinide, aliretinoin, tretinoin, bexarotene and LGD-1550.

Examples of plant alkaloids include, but are not limited to, vincristine, vinblastine, vindesine and vinorelbine.

Examples of proteasome inhibitors include, but are not limited to, bortezomib, MG-132, NPI-0052 and PR-171.

Examples of immunologicals include, but are not limited to, interferons and numerous other immune-enhancing agents. Interferons include interferon alpha, interferon alpha-2a, interferon alpha-2b, interferon beta, interferon gamma-1a, interferon gamma-1b, interferon gamma-n1 and combinations thereof. Other agents include filgrastim, lentinan, sizofilan, BCG live, ubenimex, WF-10 (tetrachlorodecaoxide or TCDO), aldesleukin, alemtuzumab, BAM-002, dacarbazine, daclizumab, denileukin, gemtuzumab ozogamicin, ibritumomab, imiquimod, lenograstim, melanoma vaccine, molgramostim, sargaramostim, tasonermin, tecleukin, thymalasin, tositumomab, Virulizin™ immunotherapeutic of Lorus Pharmaceuticals, Z-100 (specific substance of Maruyama or SSM), Zevalin™ (90Y-ibritumomab tiuxetan), epratuzumab, mitumomab, oregovomab, pemtumomab, Provenge™ (sipuleucel-T), teceleukin, Therocys™ (Bacillus Calmette-Guerin), cytotoxic lymphocyte antigen 4 (CTLA4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include, but are not limited to, krestin, lentinan, sizofuran, picibanil, PF-3512676 and ubenimex.

Examples of pyrimidine analogs include, but are not limited to, 5-fluorouracil, floxuridine, doxifluridine, raltitrexed, cytarabine, cytosine arabinoside, fludarabine, triacetyluridine, troxacitabine and gemcitabine.

Examples of purine analogs include, but are not limited to, mercaptopurine and thioguanine.

Examples of antimitotic agents include, but are not limited to, N-(2-((4-hydroxyphenyl)amino)pyridin-3-yl)-4-methoxybenzenesulfonamide, paclitaxel, docetaxel, larotaxel, epothilone D, PNU-100940, batabulin, ixabepilone, patupilone, XRP-9881, vinflunine and ZK-EPO (synthetic epothilone).

Examples of radiotherapy include, but are not limited to, external beam radiotherapy (XBRT), teletherapy, brachytherapy, sealed-source radiotherapy and unsealed-source radiotherapy.

BiTE antibodies are bi-specific antibodies that direct T-cells to attack cancer cells by simultaneously binding the two cells. The T-cell then attacks the target cancer cell. Examples of BiTE antibodies include, but are not limited to, adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (Sutton et al. (1997) *J. Immunol.* 158:5783-5790).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263 (Tse et al. (2008), supra, and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy-chain DVD polypeptides and two light-chain DVD polypeptides are referred to as DVD Ig's. Each half of a DVD Ig comprises a heavy-chain DVD polypeptide, a light-chain DVD polypeptide, and two antigen binding sites. Each binding site comprises a heavy-chain variable domain and a light-chain variable domain with a total of 6 CDRs involved in antigen binding per antigen binding site.

PARP inhibitors include, but are not limited to, ABT-888, olaparib, KU-59436, AZD-2281, AG-014699, BSI-201, BGP-15, INO-1001, ONO-2231 and the like.

Additionally or alternatively, a composition of the present invention can be administered in combination therapy with one or more antitumor agents selected from ABT-100, N-acetylcolchinol-O-phosphate, acitretin, AE-941, aglycon protopanaxadiol, arglabin, arsenic trioxide, AS04 adjuvant-adsorbed HPV vaccine, L-asparaginase, atamestane, atrasentan, AVE-8062, bosentan, canfosfamide, Canvaxin™, catumaxomab, CeaVac™, celmoleukin, combrestatin A4P, contusugene ladenovec, Cotara™, cyproterone, deoxycoformycin, dexrazoxane, N,N-diethyl-2-(4-(phenylmethyl)phenoxy)ethanamine, 5,6-dimethylxanthenone-4-acetic acid, docosahexaenoic acid/paclitaxel, discodermolide, efaproxiral, enzastaurin, epothilone B, ethynyluracil, exisulind, falimarev, Gastrimmune™, GMK vaccine, GVAX™, halofuginone, histamine, hydroxycarbamide, ibandronic acid, ibritumomab tiuxetan, IL-13-PE38, inalimarev, interleukin 4, KSB-311, lanreotide, lenalidomide, lonafarnib, lovastatin, 5,10-methylenetetrahydrofolate, mifamurtide, miltefosine, motexafin, oblimersen, OncoVAX™, Osidem™, paclitaxel albumin-stabilized nanoparticle, paclitaxel poliglumex, pamidronate, panitumumab, peginterferon alfa, pegaspargase, phenoxodiol, poly(I)-poly(C12U), procarbazine, ranpirnase, rebimastat, recombinant quadrivalent HPV vaccine, squalamine, staurosporine, STn-KLH vaccine, T4 endonuclease V, tazarotene, 6,6',7,12-tetramethoxy-2,2'-dimethyl-1β-berbaman, thalidomide, TNFerade™, $^{131}$I-tositumomab, trabectedin, triazone, tumor necrosis factor, Ukrain™, vaccinia-MUC-1 vaccine, L-valine-L-boroproline, Vitaxin™, vitespen, zoledronic acid and zorubicin.

In one embodiment, a composition of the invention is administered in a therapeutically effective amount to a subject in need thereof to treat a disease during which is overexpressed one or more of antiapoptotic Bcl-2 protein, antiapoptotic Bcl-X$_L$ protein and antiapoptotic Bcl-w protein.

In another embodiment, a composition of the invention is administered in a therapeutically effective amount to a subject in need thereof to treat a disease of abnormal cell growth and/or dysregulated apoptosis.

Examples of such diseases include, but are not limited to, cancer, mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, colon cancer, rectal cancer, cancer of the anal region, stomach cancer, gastrointestinal (gastric, colorectal and/or duodenal) cancer, chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular (hepatic and/or biliary duct) cancer, primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, non-small-cell lung cancer, prostate cancer, small-cell lung cancer, cancer of the kidney and/or ureter, renal cell carcinoma, carcinoma of the renal pelvis, neoplasms of the central nervous system, primary central nervous system lymphoma, non-Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma or a combination thereof.

In a more particular embodiment, a composition of the invention is administered in a therapeutically effective amount to a subject in need thereof to treat bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small-cell lung cancer, prostate cancer, small-cell lung cancer or spleen cancer.

According to any of these embodiments, the composition can be administered in combination therapy with one or more additional therapeutic agents.

For example, a method for treating mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, colon cancer, rectal cancer, cancer of the anal region, stomach cancer, gastrointestinal (gastric, colorectal and/or duodenal) cancer, chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular (hepatic and/or biliary duct) cancer, primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, non-small-cell lung cancer, prostate cancer, small-cell lung cancer, cancer of the kidney and/or ureter, renal cell carcinoma, carcinoma of the renal pelvis, neoplasms of the central nervous system, primary central nervous system lymphoma, non-Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma or a combination thereof in a subject comprises administering to the subject therapeutically effective amounts of (a) an ABT-263 composition of the invention and (b) one or more of etoposide, vincristine, CHOP, rituximab, rapamycin, R-CHOP, RCVP, DA-EPOCH-R or bortezomib.

In particular embodiments, a composition of the invention is administered in a therapeutically effective amount to a subject in need thereof in combination therapy with etoposide, vincristine, CHOP, rituximab, rapamycin, R-CHOP, RCVP, DA-EPOCH-R or bortezomib in a therapeutically effective amount, for treatment of a lymphoid malignancy such as B-cell lymphoma or non-Hodgkin's lymphoma.

The present invention also provides a method for maintaining in bloodstream of a human cancer patient a therapeutically effective plasma concentration of ABT-263 and/or one or more metabolites thereof, comprising administering to the subject one to a plurality of capsules as described herein, in a dosage amount equivalent to about 50 to about 500 mg ABT-263 per day, at an average dosage interval of about 3 hours to about 7 days.

What constitutes a therapeutically effective plasma concentration depends inter alia on the particular cancer present in the patient, the stage, severity and aggressiveness of the cancer, and the outcome sought (e.g., stabilization, reduction in tumor growth, tumor shrinkage, reduced risk of metastasis, etc.). It is strongly preferred that, while the plasma concentration is sufficient to provide benefit in terms of treating the cancer, it should not be sufficient to provoke an adverse side-effect to an unacceptable or intolerable degree.

EXAMPLES

The following examples are illustrative of the invention or of problems overcome by the invention, but are not to be construed as limiting. Characterization of a particular embodiment as unfavorable or not selected for preparation of a prototype formulation does not necessarily mean that such embodiment is totally inoperative or outside the scope of the invention. One of skill in the art, based on the full disclosure herein, can prepare acceptable formulations even using ingredients shown herein to be suboptimal.

Example 1

Solubility of ABT-263 Parent and Bis-HCl Salt in Lipid Solvents

Solubility of ABT-263 parent (free base, crystalline Form I) and ABT-263 bis-HCl salt was tested in a variety of lipid solvents and solvent mixtures in ambient conditions. Trademarked solvents in this study, unless identified hereinabove, are as follows (substantially equivalent products from other manufacturers can be substituted if available):

Miglyol 810™ of Sasol: caprylic/capric triglycerides;

Capmul MCM™ of Abitec: glyceryl caprylate/caprate;

Captex 300™ of Abitec: caprylic/capric triglycerides;

Labrafil M 2125 CS™ of Gattefossé: polyoxyethylene glyceryl linoleate;

Tween 20™ of Uniqema: polysorbate 20;

Labrasol™ of Gattefossé: polyoxyethylene glyceryl caprylate/caprate;

Cremophor RH40™: polyoxyethyene (40) hydrogenated castor oil.

"PE-91" is Phosal 53 MCT™+ethanol, 9:1 by volume. "LOT-343" is Labrafil M 1944 CS™+oleic acid+Tween 80™, 30:40:30 by weight.

Solubility data are presented in Table 4. In some cases, indicated in Table 4 by an asterisk (*), solubility was initially high but precipitation occurred upon standing.

TABLE 4

| Solubility (mg/g) of ABT-263 parent and bis-HCl salt in lipid solvents | | |
|---|---|---|
| Solvent | Parent (Form I) | bis-HCl salt |
| corn oil | <86 | <104 |
| sesame oil | <75 | <80 |
| castor oil | * | >78.8 |
| Miglyol 810 ™ | <76 | <84 |
| Lipoid S75 ™ MCT | 150-200 | 48.9 |
| Phosal 53 MCT ™ | >300 | n.d. |
| oleic acid | >514 | <498 |
| Imwitor 742 ™ | * | >245 |
| Capmul MCM ™ | * | >321 |
| Capmul PG-8 ™ | * | <43 |
| Capmul PG-12 ™ | * | <39 |
| Captex 300 ™ | * | <52 |
| Labrafil M 1944 CS ™ | >265 | <45 |
| Labrafil M 2125 CS ™ | >290 | <44 |
| PEG-400 | >200 | >278 |
| propylene glycol | * | >337 |
| Tween 20 ™ | >256 | >176 |
| Tween 80 ™ | >256 | >125 |
| Labrasol ™ | >242 | >292 |
| Cremophor RH40 ™ | >226 | n.d. |
| poloxamer 124 | >231 | <41 |
| PE-91 | >250 | 89 |
| LOT-343 | >479 | n.d. | n.d. not determined

Example 2

Miscibility of Ternary Excipient Systems with ABT-263 Parent and Bis-HCl Salt

Ternary systems consisting of two solvents and a surfactant were evaluated for miscibility and drug solubility using 20% by weight ABT-263 free base or 10% by weight ABT-263 bis-HCl salt. Solvents evaluated included Labrafil M 1944 CS™, Imwitor 742™, oleic acid, Capmul PG-8™, Capmul PG-12™, Lauroglycol 90™ (propylene glycol monolaurate, available from Gattefossé) and Phosal 53 MCT™. Surfactants evaluated included Tween 80™, Cremophor RH40™, Gelucire 44/14™ (polyoxyethylene glyceryl laurate, available from Gattefossé) and Labrasol™. Data are presented in Table 5.

TABLE 5

Miscibility of ternary systems and solubility of ABT-263 parent and bis-HCl salt

| Ternary system | % by weight | Miscibility of excipients | ABT-263 solubility 10% salt | 20% free base |
|---|---|---|---|---|
| Labrafil M 1944 CS ™ | 30:45:25 | ✓ | ✓ | x |
| Imwitor 742 ™ | 40:35:25 | ✓ | ✓ | x |
| Tween 80 ™ | 30:40:30 | ✓ | ✓ | x |
| (LIT systems) | 40:30:30 | ✓ | ✓ | x |
| Labrafil M 1944 CS ™ | 30:45:25 | ✓ | ✓ | ✓ |
| oleic acid | 40:35:25 | ✓ | ✓ | ✓ |
| Tween 80 ™ | 30:40:30 | ✓ | ✓ | ✓ |
| (LOT systems) | 40:30:30 | ✓ | ✓ | ✓ |
| Capmul PG-8 ™ | 45:30:25 | ✓ | x | x |
| Labrafil M 1944 CS ™ | 35:40:25 | ✓ | x | x |
| Tween 80 ™ | 40:30:30 | ✓ | x | x |
| (C8LT systems) | 30:40:30 | ✓ | x | x |
| Capmul PG-12 ™ | 45:30:25 | ✓ | ✓ | ✓ |
| Labrafil M 1944 CS ™ | 35:40:25 | ✓ | ✓ | ✓ |
| Tween 80 ™ | 40:30:30 | ✓ | ✓ | ✓ |
| (C12LT systems) | 30:40:30 | ✓ | ✓ | ✓ |
| Imwitor 742 ™ | 45:30:25 | x | N/A (vehicle not miscible) | |
| Labrafil M 1944 CS ™ | 35:40:25 | x | N/A (vehicle not miscible) | |
| Cremophor RH40 ™ | 40:30:30 | x | N/A (vehicle not miscible) | |
| (ILC systems) | 30:40:30 | x | N/A (vehicle not miscible) | |
|  | 60:30:10 | ✓ | ✓ | x |
|  | 50:40:10 | ✓ | ✓ | x |
|  | 50:30:20 | ✓ | ✓ | x |
|  | 40:40:20 | ✓ | ✓ | x |
| Labrafil M 1944 CS ™ | 30:45:25 | x | N/A (vehicle not miscible) | |
| oleic acid | 40:35:25 | x | N/A (vehicle not miscible) | |
| Cremophor RH40 ™ | 30:40:30 | x | N/A (vehicle not miscible) | |
| (LOC systems) | 40:30:30 | x | N/A (vehicle not miscible) | |
|  | 30:60:10 | ✓ | ✓ | ✓ |
|  | 40:50:10 | ✓ | ✓ | ✓ |
|  | 30:50:20 | x | N/A (vehicle not miscible) | |
|  | 40:40:20 | x | N/A (vehicle not miscible) | |
| Capmul PG-8 ™ | 45:30:25 | x | N/A (vehicle not miscible) | |
| Labrafil M 1944 CS ™ | 35:40:25 | x | N/A (vehicle not miscible) | |
| Cremophor RH40 ™ | 40:30:30 | x | N/A (vehicle not miscible) | |
| (C8LC systems) | 30:40:30 | x | N/A (vehicle not miscible) | |
|  | 60:30:10 | ✓ | x | x |
|  | 50:40:10 | ✓ | x | x |
|  | 50:30:20 | ✓ | x | x |
|  | 40:40:20 | ✓ | x | x |
| Capmul PG-12 ™ | 45:30:25 | x | N/A (vehicle not miscible) | |
| Labrafil M 1944 CS ™ | 35:40:25 | x | N/A (vehicle not miscible) | |
| Cremophor RH40 ™ | 40:30:30 | x | N/A (vehicle not miscible) | |
| (C12LC systems) | 30:40:30 | x | N/A (vehicle not miscible) | |
| Lauroglycol 90 ™ | 45:30:25 | ✓ | ✓ | ✓ |
| Labrafil M 1944 CS ™ | 35:40:25 | x | N/A (vehicle not miscible) | |
| Cremophor RH40 ™ | 40:30:30 | x | N/A (vehicle not miscible) | |
| (LLC systems) | 30:40:30 | x | N/A (vehicle not miscible) | |
| Imwitor 742 ™ | 60:30:10 | x | N/A (vehicle not miscible) | |
| Labrafil M 1944 CS ™ | 50:40:10 | x | N/A (vehicle not miscible) | |
| Gelucire 44/14 ™ | 50:30:20 | x | N/A (vehicle not miscible) | |
| (ILG systems) | 40:40:20 | x | N/A (vehicle not miscible) | |
| oleic acid | 60:30:10 | x | N/A (vehicle not miscible) | |
| Labrafil M 1944 CS ™ | 50:40:10 | x | N/A (vehicle not miscible) | |
| Gelucire 44/14 ™ | 50:30:20 | x | N/A (vehicle not miscible) | |
| (OLG systems) | 40:40:20 | x | N/A (vehicle not miscible) | |
| Capmul PG-8 ™ | 60:30:10 | x | N/A (vehicle not miscible) | |
| Labrafil M 1944 CS ™ | 50:40:10 | x | N/A (vehicle not miscible) | |
| Gelucire 44/14 | 50:30:20 | x | N/A (vehicle not miscible) | |
| (C8LG systems) | 40:40:20 | x | N/A (vehicle not miscible) | |
| Lauroglycol 90 ™ | 60:30:10 | x | N/A (vehicle not miscible) | |
| Labrafil M 1944 CS ™ | 50:40:10 | x | N/A (vehicle not miscible) | |
| Gelucire 44/14 ™ | 50:30:20 | x | N/A (vehicle not miscible) | |
| (LLG systems) | 40:40:20 | x | N/A (vehicle not miscible) | |
| Imwitor 742 ™ | 60:30:10 | ✓ | ✓ | x |
| Labrafil M 1944 CS ™ | 50:40:10 | ✓ | ✓ | x |
| Labrasol ™ | 50:30:20 | ✓ | ✓ | x |
| (ILL systems) | 40:40:20 | ✓ | ✓ | x |
| oleic acid | 60:30:10 | ✓ | ✓ | ✓ |
| Labrafil M 1944 CS ™ | 50:40:10 | ✓ | ✓ | ✓ |
| Labrasol ™ | 50:30:20 | ✓ | ✓ | ✓ |
| (OLL systems) | 40:40:20 | ✓ | ✓ | ✓ |
| Capmul PG-8 | 60:30:10 | ✓ | x | x |
| Labrafil M 1944 CS ™ | 50:40:10 | ✓ | x | x |

TABLE 5-continued

Miscibility of ternary systems and solubility of ABT-263 parent and bis-HCl salt

| Ternary system | % by weight | Miscibility of excipients | ABT-263 solubility 10% salt | 20% free base |
|---|---|---|---|---|
| Labrasol ™ | 50:30:20 | ✓ | x | x |
| (C8LL systems) | 40:40:20 | ✓ | ✓ | ✓ |
| Lauroglycol 90 ™ | 60:30:10 | ✓ | ✓ | x |
| Labrafil M 1944 CS ™ | 50:40:10 | ✓ | ✓ | x |
| Labrasol ™ | 50:30:20 | ✓ | ✓ | ✓ |
| (LLL systems) | 40:40:20 | ✓ | ✓ | ✓ |

All ternary excipient systems tested containing 10-20% Gelucire 44/14™ exhibited immiscibility. Most systems tested containing greater than 20% Cremophor RH40™ also showed immiscibility. Only in certain systems where the excipients were miscible was ABT-263 in free base or bis-HCl salt form soluble at the concentrations tested.

Data for further ternary systems containing phophatidylcholine-based excipients are presented in Example 8, Tables 10 and 11.

Example 3

Chemical Stability of ABT-263 Free Base and Bis-HCl Salt in Lipid Solution

Preliminary stability studies were conducted to allow a side-by-side comparison between lipid solutions of ABT-263 in bis-HCl salt and free base form. ABT-263 was dissolved in two separate sets of lipid vehicles, Phosal 53 MCT™/ethanol (9:1 by volume; "PE-91") and Labrafil M 1944 CS™/oleic acid/Tween 80™ (30:40:30 by weight; "LOT-343"). No antioxidant was included, nor was headspace nitrogen purging performed. After aging of samples at 40° C. (stress condition) for up to 3 weeks, analysis of total sulfoxides indicated that free base was significantly more stable than bis-HCl salt in the solutions tested (Table 6). Total degradant levels also showed a similar trend (data not shown). The increase in degradant level was accompanied by color change. The bis-HCl salt solutions upon aging showed pronounced color darkening whereas the free base solutions exhibited very little color change.

TABLE 6

Sulfoxide formation in lipid solutions of ABT-263 free base and bis-HCl salt

| | % w/w total sulfoxides | | | |
|---|---|---|---|---|
| | Solution A | | Solution B | |
| Time (weeks) | free base 25 mg/ml | bis-HCl salt 25 mg/ml | free base 100 mg/ml | bis-HCl salt 100 mg/ml |
| 0 | 0.05 | 0.07 | 2.49 | 2.24 |
| 1 | 0.27 | 0.79 | 3.70 | 7.15 |
| 2 | 0.53 | 1.90 | 4.11 | 37.52 |
| 3 | 0.84 | 3.44 | no data | no data |

Example 4

Chemical Stability of ABT-263 Free Base in Various Lipid Solutions

The chemical stability of the ABT-263 free base in solution in various lipid excipients was assessed by conducting a two-week stress test at 40° C., without antioxidant or nitrogen purging. Results are presented in Table 7.

TABLE 7

Sulfoxide formation in lipid solutions of ABT-263 free base

| | Concentration | % w/w total sulfoxides* | | |
|---|---|---|---|---|
| Lipid solvent | (mg/g) | Initial | 1 week | 2 weeks |
| Lipoid S75 ™ MCT | 100 | 0.21 | 0.33 | 0.51 |
| Imwitor 742 ™ | 25** | 0.25 | 0.20 | 0.14 |
| Capmul PG-8 ™ | 25** | 0.21 | 0.25 | 0.19 |
| Tween 80 ™ | 100 | 0.20 | 0.59 | 0.84 |
| Crillet 4HP ™ | 100 | 0.18 | 0.44 | 0.64 |
| Plurol Oleique CC497 ™*/ Lipoid S75 ™ MCT 50:50 v/v | 50 | 0.31 | 2.41 | 6.26 |
| Labrafil M 1944 CS ™ | 100 | 0.30 | 5.86 | 9.16 |
| oleic acid (super-refined) | 100 | 0.04 | 0.18 | 0.29 |
| Phosal 53 MCT ™/ethanol 9:1 v/v | 50 | n.d. | 0.14 | 0.18 |

*sulfoxide was analyzed as peak % relative to that of ABT-263
**lower concentration was used due to low drug solubility in the lipid vehicle
***polyglyceryl oleate, available from Gattefossé
n.d. not detectable The following can be summarized from the above study.

Very little or only slight growth of sulfoxides was seen in phophatidylcholine-based lipid excipients such as Phosal 53 MCT™ or Lipoid S75™ MCT.

Very little or only slight growth of sulfoxides was seen in Imwitor 742™, Capmul PG-8™ and oleic acid (super-refined grade).

Moderate sulfoxide growth was seen in Tween 80™. The degradation was slowed down when a more pure grade of polysorbate 80 (Crillet 4HP™) was used.

Labrafil M 1944 CS™ and Plurol Oleique CC497™ were both associated with significant degradation of the ABT-263. Both these excipients contain oleic acid in their structure, and the unsaturated nature of oleic acid is known to promote oxidative reaction. This may be the reason for the chemical instability of the drug in these excipients.

Example 5

Chemical Stability of ABT-263 Free Base in Ternary Lipid Solution Systems

Although ABT-263 appeared to be stable in super-refined oleic acid during the two-week stressed test of Example 4, a subsequent test using multicomponent vehicles showed that drug solutions containing oleic acid led to color change upon standing. A comparative storage study was conducted at ambient temperature using solutions of ABT-263 in Imwitor 742™/oleic acid/Tween 80™ (30:40:30 by weight; "IOT-343") and Imwitor 742™/Phosal 53 MCT™/Tween 80™ (40:40:20 by weight; "IPT-442"). The IOT-343 vehicle itself was colorless, and adding ABT-263 free base at 10% by weight to the vehicle only made it very slightly yellow-hued, but the color of the resulting ABT-263 solution darkened significantly upon storage. This was in contrast to a solution of ABT-263 free base at 10% by weight in IPT-442 solution, which had a yellow colored vehicle to begin with, but only darkened slightly upon storage. HPLC analysis for the two drug solutions after storage at ambient conditions for 3 months confirmed that the color change correlated to degradation (total sulfoxide levels were 1.3% for the IOT-343 system and 0.5% for the IPT-442 system). Therefore, oleic acid was excluded from lipid excipients to be used for ABT-263 liquid-filled capsule formulation.

Further stress testing on ABT-263 free base lipid solutions using different ternary lipid combinations showed that Labrafil M 1944 CS™ was also associated with significant oxidative degradation of ABT-263. As shown by results from a three-week stress test presented in Table 8, formulations containing Labrafil M 1944 CS™ showed significant sulfoxide growth upon storage at 40° C. without antioxidant or nitrogen purging. On the other hand, an Imwitor 742™/Phosal 53 MCT™/Tween 80™ (20:50:30 by weight; "IPT-253") solution of ABT-263 which had neither oleic acid nor Labrafil M 1944 CS™ showed much enhanced chemical stability compared to the other formulations tested, namely Labrafil M 1944 CS™/oleic acid/Tween 80™ (30:40:30 by weight; "LOT-343") and Labrafil M 1944 CS™/Imwitor 742™/Tween 80™ (40:30:30 by weight; "LIT-433"). Therefore, both Labrafil M 1944 CS™ as well as oleic acid was excluded from lipid excipients to be used for ABT-263 liquid-filled capsule formulation.

TABLE 8

Sulfoxide formation in ternary lipid solutions of ABT-263 free base

| Ternary lipid solvent system | Concentration (mg/g) | % w/w total sulfoxides* | | | |
|---|---|---|---|---|---|
| | | Initial | 1 week | 2 weeks | 3 weeks |
| LOT-343 | 100 | 2.49 | 3.70 | 4.11 | no data |
| LIT-433 | 100 | 0.21 | 3.20 | 5.13 | no data |
| LIT-433 | 150 | 0.23 | 2.28 | 3.61 | 3.80 |
| IPT-253 | 150 | n.d. | 0.26 | 0.47 | 0.56 |

*sulfoxide was analyzed as peak % relative to that of ABT-263
n.d. not detectable

Example 6

Antioxidant Testing for ABT-263 Free Base in Lipid Solution Systems

The effectiveness of different antioxidants in inhibiting oxidative degradation was evaluated in lipid solutions containing ABT-263 free base at 100 mg/g in two different lipid solution systems: (1) Lipoid S75™ MCT and (2) a ternary lipid system (LIT-433; see above). The latter was purposely chosen as a system promoting significant degradation in a short time, as an antioxidant screen. Sulfoxide formation during the two-week stress test at 40° C. with nitrogen purging is shown in Table 9.

TABLE 9

Effect of antioxidants on sulfoxide formation in solutions of ABT-263 free base

| | | % w/w total sulfoxides* | | | | | |
|---|---|---|---|---|---|---|---|
| | Antioxidant | In Lipoid S75 ™ MCT | | | In LIT-433 | | |
| Antioxidant | concentration | Initial | 1 week | 2 weeks | Initial | 1 week | 2 weeks |
| none | | 0.06 | 0.42 | 0.68 | 0.21 | 3.20 | 5.13 |
| ascorbyl palmitate | 100% molar** | n.d. | n.d. | n.d. | 0.31 | 1.37 | 2.07 |
| BHA | 100% molar** | 0.13 | 0.26 | 0.30 | 0.43 | 2.25 | 3.66 |
| BHT | 100% molar** | 0.08 | 0.17 | 0.27 | 0.37 | 2.07 | 3.40 |
| Na metabisulfite*** | 0.1% (w/w) | cloudy solution | | | 0.18 | 1.95 | 3.07 |
| Na thiosulfate*** | 0.1% (w/w) | cloudy solution | | | 0.18 | 2.64 | 4.31 |
| thioglycerol | 100% molar** | 0.08 | 0.09 | 0.13 | 0.33 | 0.50 | 0.56 |
| α-tocopherols | 145% molar** | 0.20 | 0.27 | 0.50 | 0.41 | 3.99 | 9.23 | n.d. not determined (ascorbyl palmitate could not be dissolved at 100% relative molar concentration in this solvent)
*sulfoxide was analyzed as peak % relative to that of ABT-263
**molar concentration relative to ABT-263
***an aqueous stock solution of 15% w/v was prepared for antioxidant addition.

ABT-263 free base degraded to a much lesser extent in the Lipoid S75™ MCT vehicle than in the LIT-433 vehicle system. Thioglycerol provided effective inhibition of drug oxidation in both vehicle systems. In the LIT-433 vehicle system, ascorbyl palmitate, butylated hydroxyanisole (BHA), butylated hydroxytoluene (BHT), sodium metabisulfite and sodium thiosulfate inhibited oxidative degradation to some extent at the concentrations tested, but α-tocopherols were ineffective. It is noted that the concentrations of sodium metabisulfite and sodium thiosulfate were very much lower than those providing molar equivalence to ABT-263. Even at the low concentrations used, the addition of water with these antioxidants led to cloudy solutions. The concentrations of ascorbyl palmitate, BHA and BHT were much higher than typically used for antioxidant purposes.

Example 7

BHA as an Antioxidant for ABT-263 Free Base in Ternary Lipid Solution Systems

Due to its favorable lipophilic nature and wide use in lipid system as an antioxidant, the antioxidant effectiveness of BHA was tested, at a concentration more typical for BHA, in two additional ternary vehicle systems, IPT-253 and LIT-433, containing ABT-263 at 150 mg/g. Testing was done in stress conditions at 40° C. without nitrogen purging. As shown in Table 10, in both systems, addition of 0.2% w/w BHA did not provide any inhibition of sulfoxide formation. It was concluded that free-radical-scavenger types of antioxidant such as BHA and BHT do not appear to be useful in protecting ABT-263 from oxidative degradation in lipid solutions.

TABLE 9

Effect of BHA on sulfoxide formation in solutions of ABT-263 free base

| Ternary system | Antioxidant | % w/w total sulfoxides | | | | |
|---|---|---|---|---|---|---|
| | | Initial | 1 week | 2 weeks | 3 weeks | 4 weeks |
| IPT-253 | none | n.d. | 0.26 | 0.47 | 0.56 | 0.67 |
| | 0.2% w/w BHA | 0.06 | 0.29 | 0.49 | 0.58 | 0.68 |
| LIT-433 | none | 0.23 | 2.28 | 3.61 | 3.86 | 4.19 |
| | 0.2% w/w BHA | 0.24 | 2.22 | 3.54 | 3.80 | 4.19 | n.d. not detectable

Example 8

Phospholipid Solution Systems for ABT-263 Free Base

Based on the above studies, the phosphotidylcholine-containing excipients Phosal 53 MCT™ and Lipoid S75™ MCT were concluded to provide good chemical stability and drug solubility for ABT-263 free base. However, these pre-blended excipients are not suitable for use alone as a vehicle for an ABT-263 liquid-filled capsule, due to either high viscosity (Phosal 53 MCT™) or insufficient drug solubility (Lipoid S75™ MCT). Polysorbate 80 could be used to enhance drug solubility in the vehicle. Excipients such as Capmul PG-8™ or Imwitor 742™ could be used to reduce viscosity of the lipid solution. Both were shown to be chemically compatible with ABT-263. Imwitor 742™ was preferred over Capmul PG-8™ based on previous experience in FDA approved drug products.

Consequently, in developing a prototype liquid-filled capsule, attention focused on excipients such as Phosal 53 MCT™, Lipoid S75™ MCT, polysorbate 80 (the more pure forms such as Crillet 4HP™ and super-refined Tween 80™ being preferred) and Imwitor 742™.

Two ternary lipid vehicle systems containing either Imwitor 742™/Phosal 53 MCT™/Tween 80™ (abbreviated as "IPT") systems or Imwitor 742™/Lipoid S75™ MCT/Tween 80™ (abbreviated as "IST") systems at various excipient ratios were investigated in a screen for prototype capsule formulations. The level of Imwitor 742™ in the ternary blend was limited to no more than 40%, and the level of polysorbate 80 to no more than 20%. The three-digit suffix following "IPT" or "IST" refers to the respective percentages of the three excipient ingredients, in each case omitting the final zero.

Selection of prototype formulations was based on vehicle miscibility, ABT-263 free base solubility in the vehicle, viscosity of the resulting solution (judged by severity of stringing when released from a dropper) and self-dispersing property of the drug solution (at 10% by weight drug loading), as summarized in Tables 10 and 11 for IPT and IST systems respectively. Schematic phase diagrams for IPT and IST systems (FIGS. 1 and 2) further illustrate the selection process.

Figure 2:
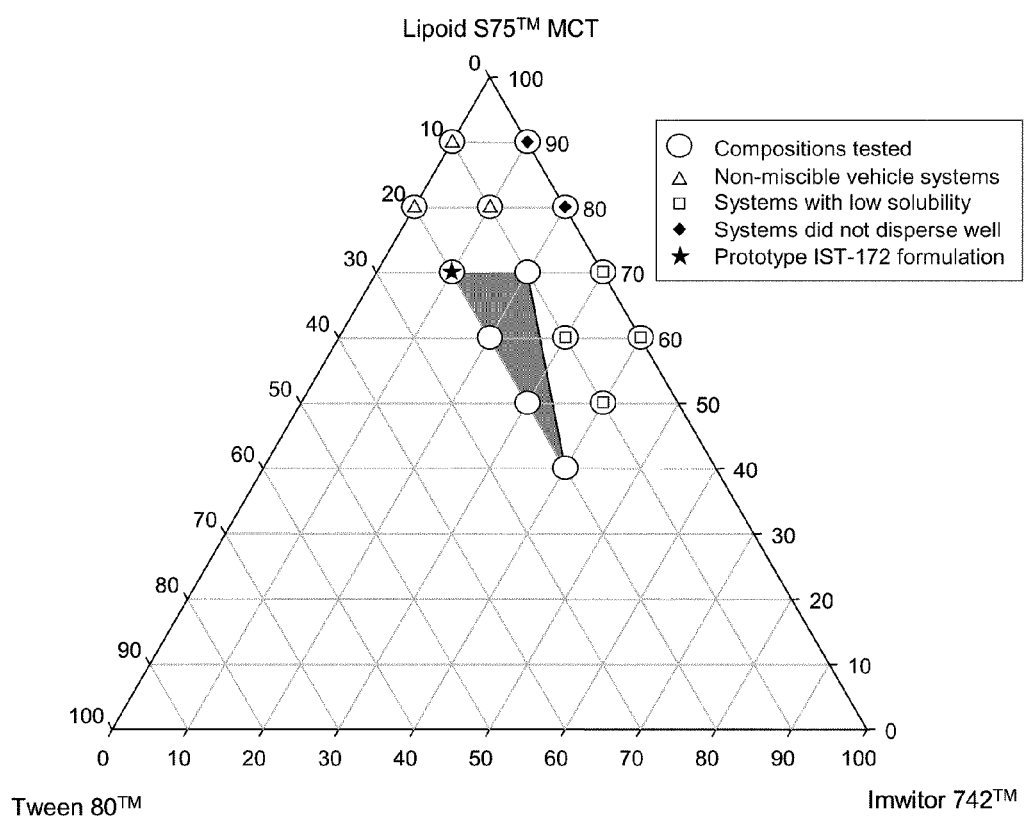
FIG. 2 is a schematic phase diagram of ABT-263 free base solutions in ternary "IST" lipid systems as described in Example 8. The shaded portion of the diagram represents an area of optimized formulation composition.

As can be seen from Tables 10 and 11 and the phase diagrams in FIGS. 1 and 2, the IPT systems in general provided better vehicle miscibility, drug solubility and dispersibility than the corresponding IST systems. IPT-262 and IST-262 (later replaced by IST-172) were selected as prototype vehicle systems, based on the following rationales.

A phosphatidylcholine-based solvent (for example in the form of Phosal 53 MCT™ or Lipoid S75™ MCT) is needed to ensure both chemical stability (and bioavailability—see below) of the capsule formulation. The amount of such solvent is virtually unlimited due to the low toxicity and high tolerance of lecithin used in oral products.

Polysorbate 80 (especially grades of high purity) is needed to facilitate drug solubility in the vehicle and to enhance self-dispersibility of the lipid formulation. Based on a typical daily dose of ABT-263 (e.g., 200-250 mg) and a maximum daily dose of polysorbate 80 (418 mg), it is reasonable to limit the level of polysorbate 80 to no more than 20% in the vehicle for a prototype formulation with 10% drug loading. Higher levels of polysorbate 80 are also unfavorable due to chemical stability considerations.

In the IPT systems, Imwitor 742™ is needed to reduce the viscosity of the final drug solution to a level that allows for machine capsule filling. In the IST system, Imwitor 742™ is also needed to enhance the miscibility of the vehicle system, since Lipoid S75™ MCT and polysorbate 80 are not miscible at all ratios. However, the amount of Imwitor 742™ is limited to no more than 20% in both prototype systems.

It will be noted from Table 11 that the IST-172 system exhibits poor vehicle miscibility. However, it was found that upon addition of ABT-263 free base the miscibility of the entire system was acceptable; thus the IST-172 formulation became an acceptable prototype liquid for encapsulation.

TABLE 10

Formulation properties of IPT systems containing 10% ABT-263 free base

| Vehicle | Vehicle miscibility | Drug solubility | Stringing* | Dispersibility (description) |
|---|---|---|---|---|
| IPT-190 | ✓ | ✓ | ++ | Dispersed with vigorous shaking |
| IPT-280 | ✓ | ✓ | ++ | Dispersed with vigorous shaking |
| IPT-370 | ✓ | ✓ | ++ | Dispersed with gentle shaking |
| IPT-460 | ✓ | ✓ | + | Dispersed with gentle shaking |
| IPT-091 | ✓ | ✓ | +++ | Dispersed with vigorous shaking |
| IPT-181 | ✓ | ✓ | ++ | Dispersed with vigorous shaking |
| IPT-271 | ✓ | ✓ | + | Dispersed with vigorous shaking |
| IPT-361 | ✓ | ✓ | + | Dispersed with vigorous shaking |
| IPT-451 | ✓ | ✓ | − | Dispersed with gentle shaking |
| IPT-082 | ✓ | ✓ | +++ | Dispersed with vigorous shaking |
| IPT-172 | ✓ | ✓ | ++ | Dispersed with gentle shaking |
| IPT-262 | ✓ | ✓ | + | Dispersed with gentle shaking |

TABLE 10-continued

Formulation properties of IPT systems containing 10% ABT-263 free base

| Vehicle | Vehicle miscibility | Drug solubility | Stringing* | Dispersibility (description) |
|---|---|---|---|---|
| IPT-352 | ✓ | ✓ | + | Dispersed with gentle shaking |
| IPT-442 | ✓ | ✓ | − | Dispersed with gentle shaking |

✓ vehicle miscible, or drug fully dissolved in vehicle
*stringing: +++ extreme; ++ significant; + slight; − none

TABLE 11

Formulation properties of IST systems containing 10% ABT-263 free base

| Vehicle | Vehicle miscibility | Drug solubility | Stringing* | Dispersibility (description) |
|---|---|---|---|---|
| IST-190 | ✓ | ✓ | − | Oil drops spread but did not disperse until shaken vigorously |
| IST-280 | ✓ | ✓ | − | Oil drops spread but did not disperse until shaken vigorously |
| IST-370 | ✓ | x | n/a | n/a |
| IST-460 | ✓ | x | n/a | n/a |
| IST-091 | x | ✓ | n/a | n/a |
| IST-181 | x | ✓ | − | Dispersed with gentle shaking |
| IST-271 | ✓ | ✓ | − | Dispersed with gentle shaking |
| IST-361 | ✓ | x | n/a | n/a |
| IST-451 | ✓ | x | n/a | n/a |
| IST-082 | x | n/a | n/a | n/a |
| IST-172 | x | ✓ | ++ | Rapidly dispersed with gentle shaking |
| IST-262 | ✓ | ✓ | + | Rapidly dispersed with gentle shaking |
| IST-352 | ✓ | ✓ | + | Dispersed with gentle shaking |
| IST-442 | ✓ | x | n/a | n/a |

✓ vehicle miscible, or drug fully dissolved in vehicle
x vehicle immiscible or miscible but turbid, or residual solids present (due to undissolved drug or precipitation)
n/a solution not made due to immiscible vehicle, or dispersibility test not performed due to undissolved drug
*stringing: +++ extreme; ++ significant; + slight; − none Example 9

Antioxidant Selection for Phospholipid-Based Solutions of ABT-263 Free Base

Based on initial antioxidant screening (see Example 6), accelerated stability studies were further conducted on the two prototype formulations using either sodium metabisulfite (NaMTBS) or thioglycerol as an antioxidant, together with 0.01% EDTA.

The solubility of neat NaMTBS in IPT-262 and IST-262 solutions containing 10% ABT-263 free base and 0.01% EDTA (as edetate calcium disodium) was assessed. After 5 days of rotary mixing under ambient temperature conditions, solids remained in all solutions, at NaMTBS solid concentrations as low as 0.05% w/w (or approximately 2% molar concentration relative to ABT-263).

Due to poor lipid solubility of NaMTBS, an alternative way of introducing it to the lipid solution is by adding a concentrated aqueous stock solution of NaMTBS to the lipid solution. For example, a clear solution was obtained when a 50 mg/ml free base solution in Phosal 53 MCT™/ethanol 9:1 v/v was spiked with a 15% w/v NaMTBS solution up to a final NaMTBS concentration of 9.67 mg/ml (or 100% molar concentration relative to ABT-263). However, as the final concentration of NaMTBS was increased to 150% relative molar concentration or higher, using the 15% w/v stock solution, the lipid solution turned turbid. Using a stock solution at a concentration greater than 20% also results in solution turbidity, indicating that both excess amounts of water and NaMTBS can lead to a cloudy solution.

Example 10

Sulfoxide Formation in Phospholipid-Based Formulations Containing Antioxidant

Results from a two-week accelerated stability study (stress condition: 40° C., with nitrogen purging), as shown in Table 12, indicated that thioglycerol is not as effective as NaMTBS in inhibiting sulfoxide formation in both prototype formulations.

However, the study results also showed that water added with the NaMTBS can negatively impact chemical stability of the drug solution, and this has been shown to be the case regardless of the ABT-263 form (free base or bis-HCl salt) or the vehicle system used (see Table 13; two-week study at 40° C., with nitrogen purging). For this reason, a final concentration of 0.05% (w/w) NaMTBS was selected, and the concentration of MTBS stock solution should also be kept below about 15% w/v in order to avoid turbidity.

TABLE 12

Sulfoxide formation in ABT-263 prototype liquids for encapsulation

| | | | % w/w total sulfoxides | | |
|---|---|---|---|---|---|
| Vehicle | Antioxidant | % water added* | Initial | 1 week | 2 weeks |
| IST-172 | none | 0 | 0.06 | 0.34 | 0.54 |
| IST-172 | 0.05% NaMTBS + 0.01% EDTA | 0.32 | 0.19 | 0.28 | 0.22 |
| IST-172 | 0.55% Thioglycerol + 0.01% EDTA | 0 | 0.22 | 0.27 | 0.55 |
| IPT-262 | none | 0 | 0.14 | 0.41 | 0.55 |
| IPT-262 | 0.05% NaMTBS + 0.01% EDTA | 0.32 | 0.43 | 0.31 | 0.23 |
| IPT-262 | 0.55% Thioglycerol + 0.01% EDTA | 0 | 0.11 | 0.26 | 0.42 |

*water as % of formulation contributed by 15% w/v NaMTBS stock solution

TABLE 13

Sulfoxide formation in ABT-263 lipid solutions: effects of NaMTBS and water

| Vehicle | ABT-263 form | ABT-263 concentration | Antioxidant | Water % | % w/w total sulfoxides |
|---|---|---|---|---|---|
| PE-91 | free base (Form I) | 50 mg/ml | none | 0 | 0.47 |
| PE-91 | free base (Form I) | 50 mg/ml | none | 3.00 | 0.66 |
| PE-91 | bis-HCl salt | 50 mg/ml | none | 0 | 1.90 |
| PE-91 | bis-HCl salt | 50 mg/ml | 0.05% NaMTBS + 0.01% EDTA | 0.32 | 0.53 |
| PE-91 | bis-HCl salt | 50 mg/ml | 0.1% NaMTBS + 0.01% EDTA | 0.61 | 0.84 |
| PE-91 | bis-HCl salt | 50 mg/ml | 0.2% NaMTBS + 0.01% EDTA | 1.17 | 0.97 |

TABLE 13-continued

Sulfoxide formation in ABT-263 lipid solutions: effects of NaMTBS and water

| Vehicle | ABT-263 form | ABT-263 concentration | Antioxidant | Water % | % w/w total sulfoxides |
|---|---|---|---|---|---|
| IST-172 | free base (Form I) | 100 mg/g | none | 0 | 0.54 |
| IST-172 | free base (Form I) | 100 mg/g | 0.05% NaMTBS + 0.01% EDTA | 0.32 | 0.22 |
| IST-172 | free base (Form I) | 100 mg/g | 0.1% NaMTBS + 0.01% EDTA | 0.61 | 0.22 |
| IST-172 | free base (Form I) | 100 mg/g | 0.2% NaMTBS + 0.01% EDTA | 1.17 | 0.58 |
| IPT-262 | free base (Form I) | 100 mg/g | none | 0 | 0.55 |
| IPT-262 | free base (Form I) | 100 mg/g | 0.05% NaMTBS + 0.01% EDTA | 0.32 | 0.23 |
| IPT-262 | free base (Form I) | 100 mg/g | 0.1% NaMTBS + 0.01% EDTA | 0.61 | 0.37 |
| IPT-262 | free base (Form I) | 100 mg/g | 0.2% NaMTBS + 0.01% EDTA | 1.17 | 0.58 |

Example 11

In vivo Pharmacokinetics of Prototype Liquid-Filled Capsules

Two 100 mg/g ABT-263 free base liquid-filled capsule prototype formulations were dosed in dogs (single-dose, non-fasting conditions) to evaluate their in vivo pharmacokinetics in comparison with 50 mg/ml oral solutions of ABT-263 free base and bis-HCl salt in Phosal 53 MCT™/ethanol 9:1 v/v with 0.01% EDTA.

Each formulation was evaluated in a group of six dogs at a dose of 50 mg/dog. Formulations A (IPT-262) and B (IST-262) were dosed in the same group of dogs in a sequential manner, and Formulations C and D were dosed in a separate group of dogs in a sequential manner. The dogs were fasted overnight prior to dosing, but food was provided 30 minutes prior to dosing. Plasma concentrations of parent drug were determined by HPLC-MS/MS at the completion of each study. Results are presented in Table 14.

The peak concentration ($C_{max}$) of formulation A in plasma was slightly lower than that of formulation B, but AUC of formulation A was higher than that of formulation B, apparently due to slower absorption. Formulation B showed a more consistent but shorter $T_{max}$ of 2-3 hours after dosing. Liquid-filled capsule formulation A gave comparable plasma $C_{max}$, AUC and bioavailability (F) to that of the oral solutions (Formulations C and D). Based on these results, the IPT-262 prototype (formulation A) was selected as a liquid-filled capsule formulation for human clinical studies.

TABLE 14

Dog pharmacokinetics of prototype liquid-filled capsules (A and B) versus comparative liquid formulations (C and D)

| Formulation | $C_{max}$ (µg/ml) | $T_{max}$ (h) | AUC (µg · h/ml) | F (%) |
|---|---|---|---|---|
| A | 9.8 | 4.7 | 98.6 | 41.9 |
| B | 11.0 | 2.5 | 76.8 | 31.8 |
| C | 11.3 | 6.0 | 107.8 | 42.5 |
| D | 11.9 | 4.5 | 94.1 | 37.7 |

Example 12

Storage Stability of Prototype Formulations with and without NaMTBS

Preliminary physical and chemical stability results have been obtained on two laboratory-scale batches of a prototype ABT-263 liquid-filled capsule formulation. The only difference between the two batches is presence or absence of antioxidant (sodium metabisulfite). Composition of the two batches is shown in Table 15.

TABLE 15

Composition of prototype liquid for capsules used in stability study

| | Batch 1 (with antioxidant) | | Batch 2 (without antioxidant) | |
|---|---|---|---|---|
| Component | mg per capsule | % w/w | mg per capsule | % w/w |
| ABT-263 free base | 50.0 | 10.0 | 50.0 | 10.0 |
| sodium metabisulfite | 0.25 | 0.05 | — | — |
| edetate calcium disodium | 0.025 | 0.005 | 0.025 | 0.005 |
| water* | 2.48 | 0.50 | 0.23 | 0.05 |
| Phosal 53 MCT ™ | 268.35 | 53.67 | 269.85 | 53.97 |
| Mono- and dicaprylic/capric glycerides | 89.45 | 17.89 | 89.95 | 17.99 |
| polysorbate 80 | 89.45 | 17.89 | 89.95 | 17.99 |
| Total | 500.0 | 100.0 | 500.0 | 100.0 |

*includes water added with sodium metabisulfite and edetate calcium disodium only The liquids having the composition shown in Table 15 were encapsulated in size 0 hard gelatin capsules and the capsules placed in blister packaging (Honeywell Aclar™ UltRx 3000 polychlorotrifluoroethylene barrier film with push-through foil lidding) for a chemical stability study. Data after one month storage under various conditions are presented in Table 16. Water content shown in Table 16 is as determined by analysis, and is not directly related to amount of water added with NaMTBS and edetate calcium disodium as in Table 15.

TABLE 16

Chemical stability results for prototype capsules with and without antioxidant

| | | Initial | | | 1 month | | |
|---|---|---|---|---|---|---|---|
| Batch | Storage conditions | total sulfoxides | total degradants | water content (%)* | total sulfoxides | total degradants | water content (%) |
| 1 (with antioxidant) | 5° C. | n.d. | 0.03% | 2.7 | n.d. | 0.03% | 3.1 |
| | 25° C. 60% RH | n.d. | 0.03% | 2.7 | n.d. | 0.06% | 3.6 |

TABLE 16-continued

Chemical stability results for prototype capsules with and without antioxidant

| Batch | Storage conditions | Initial | | | 1 month | | |
|---|---|---|---|---|---|---|---|
| | | total sulfoxides | total degradants | water content (%)* | total sulfoxides | total degradants | water content (%) |
| | 40° C. 75% RH | n.d. | 0.03% | 2.7 | n.d. | 0.03% | 4.8 |
| 2 (without antioxidant) | 5° C. | 0.08% | 0.14% | 3.2 | 0.12% | 0.17% | 3.3 |
| | 25° C. 60% RH | 0.08% | 0.14% | 3.2 | 0.08% | 0.11% | 3.1 |
| | 40° C. 75% RH | 0.08% | 0.14% | 3.2 | 0.29% | 0.42% | 3.8 |

*Initial water content of fill solution: 0.4% for batch 1; 0.2% for batch 2
n.d. not detectable It can be seen from Table 16 that addition of the antioxidant sodium metabisulfite significantly inhibited formation of total sulfoxides during the first month of storage, especially under stress storage conditions of 40° C. and 75% RH.

Data for total sulfoxides following up to six months' storage are presented in Table 17. Formation of total sulfoxides was inhibited for at least 6 months, except under stress storage conditions of 40° C. and 75% RH.

TABLE 17

Total sulfoxides in prototype capsules with and without antioxidant

| Batch | Storage conditions | Initial | 1 month | 3 months | 6 months |
|---|---|---|---|---|---|
| 1 (with antioxidant) | 5° C. | n.d. | n.d. | n.d. | n.d. |
| | 25° C. 60% RH | n.d. | n.d. | n.d. | 0.15% |
| | 40° C. 75% RH | n.d. | n.d. | no data | 1.90% |
| 2 (without antioxidant) | 5° C. | 0.08% | 0.12% | 0.11% | 0.13% |
| | 25° C. 60% RH | 0.08% | 0.08% | 0.18% | 0.28% |
| | 40° C. 75% RH | 0.08% | 0.29% | 0.91% | 1.40% | n.d. not detectable

Example 13

Storage Stability of Prototype Formulations with and without NaMTBS

A nine-months storage-stability study was conducted on the same two laboratory-scale batches of a prototype ABT-263 liquid-filled capsule formulation as described in Example 12. Again, the only difference between the two batches is presence or absence of antioxidant (sodium metabisulfite). Composition of the two batches is shown in Table 15.

For this study, the capsules were placed in 3 ounce HDPE (high-density polyethylene) bottles with child-resistant polypropylene caps, and the bottles were induction-sealed. Data for total sulfoxides are presented in Table 18. Formation of total sulfoxides was inhibited for at least 6 months, except under stress storage conditions of 40° C. and 75% RH.

TABLE 18

Total sulfoxides in prototype capsules with and without antioxidant

| Batch | Storage conditions | Initial | 3.8 months | 6 months | 9 months |
|---|---|---|---|---|---|
| 1 (with antioxidant) | 5° C. | n.d. | n.d. | n.d. | n.d. |
| | 25° C. 60% RH | n.d. | n.d. | 0.08% | 0.20% |
| | 40° C. 75% RH | n.d. | 0.51% | 1.00% | 1.74% |
| 2 (without antioxidant) | 5° C. | 0.08% | 0.10% | 0.12% | 0.16% |
| | 25° C. 60% RH | 0.08% | 0.18% | 0.27% | 0.42% |
| | 40° C. 75% RH | 0.08% | 0.75% | 1.45% | 2.25% | n.d. not detectable

Example 14

Human in vivo Pharmacokinetics of a Prototype Liquid-Filled Capsule

In vivo pharmacokinetics of a 50 mg ABT-263 prototype liquid-filled capsule (Batch 1 as described in Table 15 above) were studied in human cancer patient volunteers in comparison with a 25 mg/ml lipid solution of ABT-263 bis-HCl salt in Phosal 53 MCT™/ethanol 9:1 v/v with 0.01% EDTA. To evaluate food effect, the liquid-filled capsule was administered to fasting subjects and to subjects receiving a high-fat meal.

Figure 3:
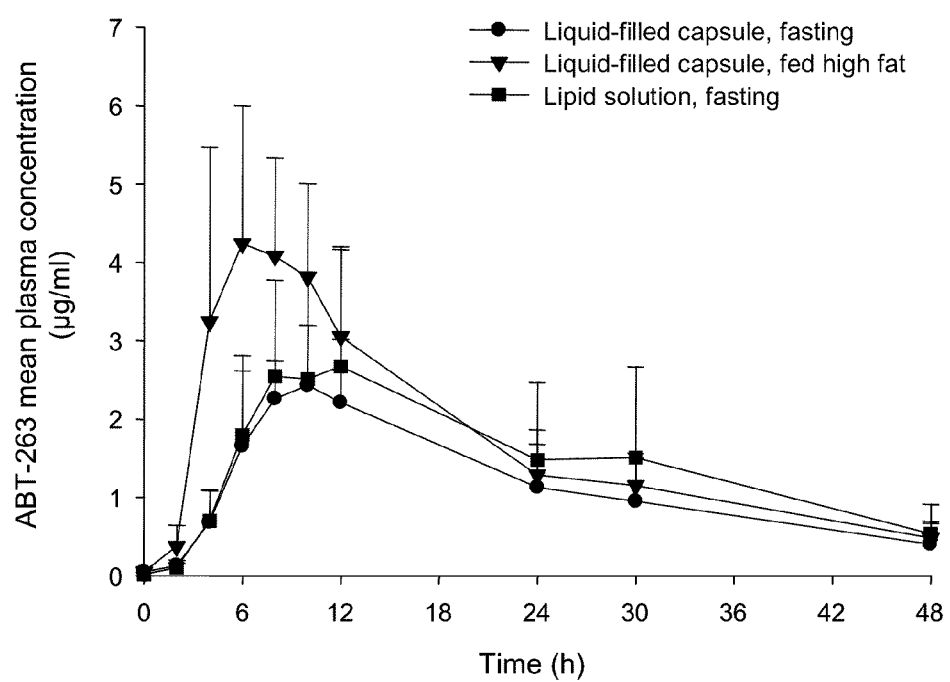
FIG. 3 is a graph of ABT-263 mean plasma concentration following administration to human cancer patients of a liquid-filled capsule of the invention by comparison with a lipid solution formulation as described in Example 14.

A randomized, 3-period crossover study design in 7 subjects was used. A total of 6 subjects completed all three periods and were considered evaluable. Each formulation was administered orally in a single dose of 200 mg ABT-263 parent-compound equivalent. Plasma samples were collected immediately before dosing and at 2, 4, 6, 8, 10, 12, 24, 30 and 48 hours after dosing. Concentrations of parent drug in the plasma samples were determined by HPLC-MS/MS at the completion of the study. Data (mean of 6 evaluable subjects) are presented in FIG. 3. Calculated pharmacokinetic parameters are shown in Table 19.

TABLE 19

Pharmacokinetic parameters (mean ± standard deviation; N = 6)

| | Lipid solution (fasting) | Liquid-filled capsule (fasting) | Liquid-filled capsule (fed high fat) |
|---|---|---|---|
| $C_{max}$ (μg/ml) | 3.30 ± 1.06 | 2.74 ± 0.68 | 4.85 ± 1.70 |
| $T_{max}$ (h) | 14.0 ± 8.0 | 9.3 ± 2.4 | 7.0 ± 2.4 |
| $AUC_{0-48}$ (μg · h/ml) | 70.2 ± 35.2 | 55.0 ± 20.8 | 82.5 ± 24.5 |
| $AUC_{0-\infty}$ (μg · h/ml) | 80.7 ± 41.3 | 63.7 ± 27.7 | 93.2 ± 26.2 |
| $t_{1/2}$ (h) | 12.8 ± 3.5 | 12.8 ± 3.1 | 14.7 ± 2.5 |

What is claimed is:

1. A pharmaceutical capsule comprising a capsule shell having encapsulated therewithin, in an amount not greater than about 1000 mg per capsule, a liquid solution of ABT-263 or a pharmaceutically acceptable salt thereof at an ABT-263 free-base equivalent concentration of at least about 40 mg/ml in a substantially non-ethanolic carrier that comprises as pharmaceutically acceptable excipients
   (a) at least one phospholipid,
   (b) at least one solubilizing agent for the at least one phospholipid, selected from the group consisting of glycols, glycolides, glycerides and mixtures thereof,
   (c) at least one non-phospholipid surfactant, and
   (d) at least one sulfur-containing antioxidant in an amount effective to reduce oxidative degradation of ABT-263 upon storage.

2. The capsule of claim 1, wherein the ABT-263 is present in free-base form.

3. The capsule of claim 2, wherein said excipients are selected and included in amounts effective to maintain in solution at least about 40 mg ABT-263 free base per capsule.

4. The capsule of claim 1, wherein the amount of said encapsulated liquid solution is about 300 to about 600 mg per capsule.

5. The capsule of claim 1, wherein the at least one phospholipid comprises phosphatidylcholine.

6. The capsule of claim 1, wherein the at least one solubilizing agent comprises one or more medium-chain triglycerides.

7. The capsule of claim 6, wherein the at least one solubilizing agent further comprises one or more medium-chain mono- and/or diglycerides.

8. The capsule of claim 1, wherein the at least one non-phospholipid surfactant comprises one or more polysorbates.

9. The capsule of claim 8, wherein the one or more polysorbates have a peroxide value of less than about 5.

10. The capsule of claim 1, wherein the at least one sulfur-containing antioxidant is poorly lipid-soluble and the encapsulated liquid solution comprises water in an amount up to about 1% by weight sufficient for introduction of the antioxidant as an aqueous stock solution.

11. The capsule of claim 10, wherein the at least one poorly lipid-soluble antioxidant is present in an amount of about 0.02% to about 0.2% by weight of the encapsulated liquid solution.

12. The capsule of claim 10, wherein the at least one poorly lipid-soluble antioxidant is selected from the group consisting of sulfites, bisulfites, metabisulfites, thiosulfates and mixtures thereof.

13. The capsule of claim 10, wherein the at least one poorly lipid-soluble antioxidant comprises sodium or potassium metabisulfite.

14. The capsule of claim 10, further comprising at least one pharmaceutically acceptable chelating agent.

15. The capsule of claim 14, wherein the at least one chelating agent comprises EDTA or a salt thereof.

16. The capsule of claim 1, wherein the encapsulated liquid solution comprises about 5% to about 20% by weight ABT-263 free base, about 15% to about 60% by weight phosphatidylcholine, about 7% to about 30% by weight medium-chain triglycerides, about 7% to about 30% by weight medium-chain mono- and diglycerides, about 7% to about 30% polysorbate 80 surfactant, about 0.02% to about 0.2% by weight sodium or potassium metabisulfite, about 0.003% to about 0.01% EDTA or salt thereof, and about 0.2% to about 0.8% water.

17. The capsule of claim 1, wherein the encapsulated liquid solution consists essentially of about 5% to about 20% by weight ABT-263 free base, about 15% to about 60% by weight phosphatidylcholine, about 7% to about 30% by weight medium-chain triglycerides, about 7% to about 30% by weight medium-chain mono- and diglycerides, about 7% to about 30% polysorbate 80 surfactant, about 0.02% to about 0.2% by weight sodium or potassium metabisulfite, about 0.003% to about 0.01% EDTA or salt thereof, and about 0.2% to about 0.8% water.

18. The capsule of claim 1, wherein the excipients are selected to provide oral bioavailability of ABT-263 of at least about 30% when administered as a single dose of about 50 mg in a fasting or non-fasting dog model.

19. A process for preparing the capsule of claim 10, comprising dissolving an API (active pharmaceutical ingredient) that consists essentially of the ABT-263 or salt thereof in at least the phospholipid and solubilizing agent to provide a lipid solution, admixing the non-phospholipid surfactant with the solubilizing agent or lipid solution, dissolving the poorly lipid-soluble sulfur-containing antioxidant in water to prepare an aqueous stock solution, admixing the aqueous stock solution with the lipid solution to provide a liquid solution for encapsulation, and encapsulating the liquid solution in a capsule shell.

20. The process of claim 19, wherein the phospholipid and at least a portion of the solubilizing agent are supplied as a pre-blended product.

21. The process of claim 20, wherein the phospholipid comprises phosphatidylcholine and the solubilizing agent pre-blended therewith comprises medium-chain triglycerides.

22. The process of claim 21, wherein the pre-blended product comprises about 50% to about 75% phosphatidylcholine and about 15% to about 30% medium-chain triglycerides.

23. The process of claim 19, wherein the API consists essentially of Form I or Form II ABT-263 crystalline free base.

24. A method for treating a disease characterized by apoptotic dysfunction and/or overexpression of an anti-apoptotic Bcl-2 family protein, comprising orally administering to a subject having the disease a therapeutically effective amount of ABT-263 formulated as the capsule of claim 1.

25. The method of claim 24, wherein the disease is a neoplastic disease.

26. The method of claim 25, wherein the neoplastic disease is selected from the group consisting of cancer, mesothelioma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, colon cancer, rectal cancer, cancer of the anal region, stomach cancer, gastrointestinal (gastric, colorectal and/or duodenal) cancer, chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular (hepatic and/or biliary duct) cancer, primary or secondary central nervous system tumor, primary or secondary brain tumor, Hodgkin's disease, chronic or acute leukemia, chronic myeloid leukemia, lymphocytic lymphoma, lymphoblastic leukemia, follicular lymphoma, lymphoid malignancies of T-cell or B-cell origin, melanoma, multiple myeloma, oral cancer, non-small-cell lung cancer, prostate cancer, small-cell lung cancer, cancer of the kidney and/or ureter, renal cell carcinoma, carcinoma of the renal pelvis, neoplasms of the central nervous system, primary central nervous system lymphoma, non-Hodgkin's lymphoma, spinal axis tumors, brain stem glioma, pituitary adenoma, adrenocortical cancer, gall bladder cancer, cancer of the spleen, cholangiocarcinoma, fibrosarcoma, neuroblastoma, retinoblastoma and combinations thereof.

27. The method of claim 25, wherein the neoplastic disease is a lymphoid malignancy.

28. The method of claim 27, wherein the lymphoid malignancy is non-Hodgkin's lymphoma.

29. The method of claim 25, wherein the neoplastic disease is chronic lymphocytic leukemia or acute lymphocytic leukemia.

30. The method of claim 24, wherein one to a plurality of said capsule is administered in a dose of about 50 to about 500 mg ABT-263 free-base equivalent per day at an average treatment interval of about 3 hours to about 7 days.

31. The method of claim 30, wherein one to a plurality of said capsule is administered once daily in a dose of about 200 to about 400 mg ABT-263 free-base equivalent per day.

32. The method of claim 31, wherein said capsule is (a) a prototype capsule comprising a size 0 hard gelatin capsule shell having encapsulated therewithin a liquid solution that comprises about 50 mg ABT-263 free base, about 150 mg phosphatidylcholine, about 75 mg medium-chain triglycerides, about 90 mg medium-chain mono- and diglycerides, about 90 mg polysorbate 80 surfactant, about 0.25 mg sodium or potassium metabisulfite, about 0.025% EDTA or salt thereof, and about 2.5 mg water; or (b) a capsule that is orally substantially bioequivalent to said prototype capsule.

33. A method for maintaining in bloodstream of a human subject a therapeutically effective plasma concentration of ABT-263 and/or one or more metabolites thereof, comprising orally administering to the subject one to a plurality of the capsule of claim 1, in a dose of about 50 to about 500 mg ABT-263 free-base equivalent per day at an average treatment interval of about 3 hours to about 7 days.

34. The method of claim 33, wherein the plasma concentration maintained exhibits, at steady state, a peak of about 3 to about 8 µg/ml ABT-263 and a trough of about 1 to about 5 µg/ml ABT-263.

35. The method of claim 33, wherein said capsule is (a) a prototype capsule comprising a size 0 hard gelatin capsule shell having encapsulated therewithin a liquid solution that comprises about 50 mg ABT-263 free base, about 150 mg phosphatidylcholine, about 75 mg medium-chain triglycerides, about 90 mg medium-chain mono- and diglycerides, about 90 mg polysorbate 80 surfactant, about 0.25 mg sodium or potassium metabisulfite, about 0.025% EDTA or salt thereof, and about 2.5 mg water; or (b) a capsule that is orally substantially bioequivalent to said prototype capsule.

36. The capsule of claim 1, wherein the water concentration does not exceed about 1% by weight of the encapsulated liquid solution.

* * * * *